(12) United States Patent
Barnes et al.

(10) Patent No.: US 12,251,122 B2
(45) Date of Patent: Mar. 18, 2025

(54) CUTTING DEVICE FOR TRIGGER FINGER AND OTHER SOFT TISSUES

(71) Applicant: Sonex Health, Inc., Eagan, MN (US)

(72) Inventors: Darryl E. Barnes, Eagan, MN (US); Jay Smith, Byron, MN (US); Aaron Keenan, Austin, MN (US); Kevin Arnal, Excelsior, MN (US)

(73) Assignee: Sonex Health, Inc., Eagan, MN (US)

( * ) Notice: Subject to any disclaimer, the term of this patent is extended or adjusted under 35 U.S.C. 154(b) by 385 days.

(21) Appl. No.: 17/733,532

(22) Filed: Apr. 29, 2022

(65) Prior Publication Data
US 2022/0346819 A1    Nov. 3, 2022

Related U.S. Application Data

(63) Continuation-in-part of application No. 29/803,594, filed on Aug. 13, 2021, now Pat. No. Des. 989,961.
(Continued)

(51) Int. Cl.
*A61B 17/32* (2006.01)
*A61B 17/00* (2006.01)

(52) U.S. Cl.
CPC ........ *A61B 17/32* (2013.01); *A61B 17/00234* (2013.01); *A61B 2017/0042* (2013.01);
(Continued)

(58) Field of Classification Search
CPC .............. A61B 17/32; A61B 17/00234; A61B 2017/0042; A61B 2017/00743; A61B 2017/32002; A61B 17/320036
See application file for complete search history.

(56) References Cited

U.S. PATENT DOCUMENTS

| 2,123,768 A | 7/1938 | Corsico-Piccolini et al. |
| 3,435,826 A | 4/1969 | Fogarty |

(Continued)

FOREIGN PATENT DOCUMENTS

| DE | 4444166 A1 | 6/1996 |
| EP | 3278749 A1 | 2/2018 |

(Continued)

OTHER PUBLICATIONS

International Search Report and Written Opinion dated Aug. 4, 2022 for International Application No. PCT/US2022/027039.
(Continued)

*Primary Examiner* — Shaun L David
*Assistant Examiner* — Rachael L Geiger
(74) *Attorney, Agent, or Firm* — Seager, Tufte & Wickhem LLP

(57) ABSTRACT

A method of cutting soft tissue in a hand to treat trigger finger involves advancing an introducer shaft into the hand to position a distal end of the introducer shaft beyond a pulley in a finger of the hand, advancing a blade along a guiding channel on an upper surface of the introducer shaft, to position a distal end of the blade at or near the distal end of the introducer shaft, and rotating a cutting surface of the blade to an orientation at or near perpendicular relative to the upper surface of the introducer shaft. The method further involves retracting the blade along the introducer shaft to cut the pulley and removing the introducer shaft and the blade from the hand.

10 Claims, 33 Drawing Sheets

Related U.S. Application Data

(60) Provisional application No. 63/232,863, filed on Aug. 13, 2021, provisional application No. 63/231,029, filed on Aug. 9, 2021, provisional application No. 63/182,259, filed on Apr. 30, 2021.

(52) U.S. Cl.
CPC ............... *A61B 2017/00743* (2013.01); *A61B 2017/320052* (2013.01)

(56) References Cited

U.S. PATENT DOCUMENTS

| | | | |
|---|---|---|---|
| 4,962,770 A | 10/1990 | Agee et al. | |
| 4,963,147 A | 10/1990 | Agee et al. | |
| 4,979,951 A | 12/1990 | Simpson | |
| 5,089,000 A | 2/1992 | Agee et al. | |
| 5,125,927 A | 6/1992 | Belanger | |
| 5,217,007 A | 6/1993 | Ciaglia | |
| 5,306,284 A | 4/1994 | Agee et al. | |
| 5,325,883 A | 7/1994 | Orr | |
| 5,345,927 A | 9/1994 | Bonutti | |
| 5,353,812 A | 10/1994 | Chow | |
| 5,425,355 A | 6/1995 | Kulick | |
| 5,480,408 A | 1/1996 | Chow | |
| 5,569,283 A | 10/1996 | Green et al. | |
| 5,620,446 A | 4/1997 | McNamara et al. | |
| 5,649,946 A | 7/1997 | Bramlet | |
| 5,655,545 A | 8/1997 | Johnson et al. | |
| 5,690,663 A | 11/1997 | Stephens | |
| 5,690,664 A | 11/1997 | Sauer et al. | |
| 5,702,417 A | 12/1997 | Hermann | |
| 5,707,382 A | 1/1998 | Sierocuk et al. | |
| 5,709,697 A | 1/1998 | Ratcliff et al. | |
| 5,735,865 A | 4/1998 | Schaumann et al. | |
| 5,755,732 A | 5/1998 | Green et al. | |
| 5,766,198 A | 6/1998 | Li | |
| 5,769,865 A | 6/1998 | Kermode et al. | |
| 5,769,895 A | 6/1998 | Ripamonti | |
| 5,772,680 A | 6/1998 | Kieturakis et al. | |
| 5,779,053 A | 7/1998 | Partika et al. | |
| 5,782,850 A | 7/1998 | Ro | |
| 5,782,854 A | 7/1998 | Hermann | |
| 5,800,449 A | 9/1998 | Wales | |
| 5,810,806 A | 9/1998 | Ritchart et al. | |
| 5,813,977 A | 9/1998 | Hinchliffe et al. | |
| 5,827,311 A | 10/1998 | Berelsman et al. | |
| 5,860,997 A | 1/1999 | Bonutti | |
| 5,865,728 A | 2/1999 | Moll et al. | |
| 5,893,861 A | 4/1999 | Yumoto | |
| 5,904,699 A | 5/1999 | Schwemberger et al. | |
| 5,908,433 A | 6/1999 | Eager et al. | |
| 5,954,739 A | 9/1999 | Bonutti | |
| 5,957,944 A | 9/1999 | Khuri et al. | |
| 5,968,061 A | 10/1999 | Mirza | |
| 6,004,337 A | 12/1999 | Kieturakis et al. | |
| 6,007,554 A | 12/1999 | Van Ess | |
| 6,012,586 A | 1/2000 | Misra | |
| 6,015,421 A | 1/2000 | Echeverry et al. | |
| 6,017,536 A | 1/2000 | Barney et al. | |
| 6,019,774 A | 2/2000 | Weiss et al. | |
| 6,030,402 A | 2/2000 | Thompson et al. | |
| 6,080,175 A | 6/2000 | Hogendijk | |
| 6,083,177 A | 7/2000 | Kobren et al. | |
| 6,106,496 A | 8/2000 | Amnissolle | |
| 6,113,617 A | 9/2000 | Van Der Merwe | |
| 6,117,153 A | 9/2000 | Lary et al. | |
| 6,168,608 B1 | 1/2001 | Echeverry et al. | |
| 6,171,236 B1 | 1/2001 | Bonutti | |
| 6,179,852 B1 | 1/2001 | Strickland et al. | |
| 6,217,602 B1 | 4/2001 | Redmon | |
| 6,258,113 B1 | 7/2001 | Adams et al. | |
| 6,264,604 B1 | 7/2001 | Kieturakis et al. | |
| 6,346,085 B1 | 2/2002 | Schiffman | |
| 6,358,251 B1 | 3/2002 | Mirza | |
| 6,361,543 B1 | 3/2002 | Chin et al. | |
| 6,402,770 B1 | 6/2002 | Jessen | |
| 6,447,529 B2 | 9/2002 | Fogarty et al. | |
| 6,451,042 B1 | 9/2002 | Bonutti | |
| 6,514,272 B1 | 2/2003 | Kieturakis et al. | |
| 6,565,590 B2 | 5/2003 | Kieturakis et al. | |
| 6,592,602 B1 | 7/2003 | Peartree et al. | |
| 6,632,234 B2 | 10/2003 | Kieturakis et al. | |
| 6,685,717 B1 | 2/2004 | Ilic | |
| 6,746,465 B2 | 6/2004 | Diederich et al. | |
| 6,875,183 B2 | 4/2005 | Cervi | |
| 6,896,141 B2 | 5/2005 | McMichael et al. | |
| 7,001,405 B2 | 2/2006 | Kieturakis et al. | |
| 7,037,317 B2 | 5/2006 | Hermann et al. | |
| 7,214,236 B2 | 5/2007 | Kieturakis et al. | |
| 7,329,253 B2 | 2/2008 | Brounstein et al. | |
| 7,331,462 B2 | 2/2008 | Steppe | |
| 7,434,687 B2 | 10/2008 | Itou et al. | |
| 7,476,235 B2 | 1/2009 | Diederich et al. | |
| 7,481,817 B2 | 1/2009 | Sauer | |
| 7,504,875 B2 | 3/2009 | Bhushan et al. | |
| 7,520,886 B2 | 4/2009 | Surti | |
| 7,628,798 B1 | 12/2009 | Welborn | |
| 7,708,751 B2 | 5/2010 | Hughes et al. | |
| 7,744,617 B2 | 6/2010 | Lunsford et al. | |
| 7,780,690 B2 | 8/2010 | Rehnke | |
| 7,918,784 B2 | 4/2011 | Wellborn et al. | |
| 7,967,137 B2 | 6/2011 | Fulbrook et al. | |
| D645,147 S | 9/2011 | Ruf | |
| 8,052,710 B2 | 11/2011 | Kambin et al. | |
| 8,105,342 B2 | 1/2012 | Onuki et al. | |
| 8,147,487 B2 | 4/2012 | Burbank et al. | |
| 8,177,064 B2 | 5/2012 | McCormick et al. | |
| 8,246,646 B2 | 8/2012 | Kambin et al. | |
| 8,252,013 B2 | 8/2012 | Leibowitz et al. | |
| D666,725 S | 9/2012 | McCormack et al. | |
| 8,257,379 B2 | 9/2012 | Lee | |
| 8,273,098 B2 | 9/2012 | Strickland | |
| 8,282,665 B2 | 10/2012 | Kieturakis et al. | |
| 8,323,278 B2 | 12/2012 | Brecheen et al. | |
| D673,683 S | 1/2013 | McCormack et al. | |
| D674,489 S | 1/2013 | McCormack et al. | |
| 8,348,966 B2 | 1/2013 | McCormack et al. | |
| 8,419,728 B2 | 4/2013 | Klotz et al. | |
| 8,449,478 B2 | 5/2013 | Lee et al. | |
| 8,500,770 B2 | 8/2013 | Echevery et al. | |
| 8,523,891 B2 | 9/2013 | Welborn | |
| 8,579,930 B2 | 11/2013 | Palmer et al. | |
| 8,603,124 B1 | 12/2013 | Hatch | |
| 8,603,738 B2 | 12/2013 | Condeelis et al. | |
| 8,608,738 B2 | 12/2013 | Brecheen et al. | |
| 8,608,763 B1 * | 12/2013 | Jurbala | A61B 17/320036 606/170 |
| 8,613,745 B2 | 12/2013 | Bleich | |
| 8,652,157 B2 | 2/2014 | McCormack et al. | |
| 8,672,960 B2 | 3/2014 | Briganti et al. | |
| 8,702,654 B2 | 4/2014 | Agee et al. | |
| 8,721,668 B2 | 5/2014 | McCormack et al. | |
| 8,746,452 B2 | 6/2014 | Tomes et al. | |
| 8,753,364 B2 | 6/2014 | McCormack et al. | |
| 8,876,845 B2 | 11/2014 | Suddaby | |
| 8,906,040 B2 | 12/2014 | Filipi et al. | |
| 8,911,470 B2 | 12/2014 | Mirza et al. | |
| 8,951,273 B1 | 2/2015 | Fard | |
| 8,992,424 B2 | 3/2015 | Orbay et al. | |
| 9,017,354 B2 | 4/2015 | Fink et al. | |
| 9,028,516 B2 | 5/2015 | Palmer et al. | |
| 9,050,004 B2 | 6/2015 | Diao et al. | |
| D735,330 S | 7/2015 | Rydberg et al. | |
| D735,332 S | 7/2015 | Allen et al. | |
| 9,113,953 B2 | 8/2015 | Smith | |
| 9,131,951 B2 | 9/2015 | Mirza et al. | |
| 9,168,057 B2 | 10/2015 | Poulsen | |
| 9,186,217 B2 | 11/2015 | Goyal | |
| D745,675 S | 12/2015 | Jankowski et al. | |
| 9,532,847 B2 | 1/2017 | Hendrickson et al. | |
| 10,206,703 B2 | 2/2019 | Palmer et al. | |
| 10,245,062 B2 | 4/2019 | Seymour | |
| 10,383,609 B2 | 8/2019 | Nakanishi et al. | |

(56) References Cited

U.S. PATENT DOCUMENTS

| | | |
|---|---|---|
| 10,413,313 B2 | 9/2019 | Brown et al. |
| D864,388 S | 10/2019 | Barber |
| 10,575,867 B2 | 3/2020 | Mirza et al. |
| 10,918,410 B2 | 2/2021 | Mirza et al. |
| 11,006,970 B2 | 5/2021 | Mirza et al. |
| 11,096,710 B2 | 8/2021 | Mirza et al. |
| 11,096,720 B2 | 8/2021 | Mirza et al. |
| 11,259,837 B2 | 3/2022 | Aklog et al. |
| D969,316 S | 11/2022 | Milhous et al. |
| D974,561 S | 1/2023 | Walsh |
| 2002/0120211 A1 | 8/2002 | Wardle et al. |
| 2002/0161387 A1 | 10/2002 | Blanco |
| 2002/0185406 A1 | 12/2002 | Massengale et al. |
| 2004/0143280 A1 | 7/2004 | Suddaby |
| 2004/0195131 A1 | 10/2004 | Spolidoro |
| 2005/0209624 A1 | 9/2005 | Vijay |
| 2005/0222598 A1 | 10/2005 | Ho et al. |
| 2005/0228426 A1 | 10/2005 | Campbell |
| 2006/0149136 A1 | 7/2006 | Seto et al. |
| 2006/0190021 A1 | 8/2006 | Hausman et al. |
| 2007/0083225 A1 | 4/2007 | Kiser et al. |
| 2007/0112366 A1 | 5/2007 | Welborn et al. |
| 2007/0118170 A1 | 5/2007 | Kieturakis et al. |
| 2007/0225740 A1 | 9/2007 | Suddaby |
| 2008/0033466 A1 | 2/2008 | Assell et al. |
| 2008/0058588 A1 | 3/2008 | Emanuel |
| 2008/0058846 A1 | 3/2008 | Vosough |
| 2008/0109021 A1 | 5/2008 | Medoff |
| 2008/0195128 A1 | 8/2008 | Orbay et al. |
| 2008/0234713 A1 | 9/2008 | Bernardini |
| 2008/0288041 A1 | 11/2008 | Holman et al. |
| 2009/0048620 A1 | 2/2009 | Weiss et al. |
| 2009/0048623 A1 | 2/2009 | Lafosse et al. |
| 2009/0125044 A1 | 5/2009 | Lary |
| 2009/0171157 A1 | 7/2009 | Diederich et al. |
| 2009/0312740 A1 | 12/2009 | Kim et al. |
| 2009/0312807 A1 | 12/2009 | Boudreault et al. |
| 2010/0010530 A1 | 1/2010 | Rhee |
| 2010/0100114 A1 | 4/2010 | Berger |
| 2010/0125266 A1 | 5/2010 | Deem et al. |
| 2010/0185222 A1 | 7/2010 | Keller |
| 2010/0211082 A1 | 8/2010 | Sauer |
| 2010/0249719 A1 | 9/2010 | Fojtik |
| 2011/0087258 A1 | 4/2011 | Sluss |
| 2011/0112563 A1 | 5/2011 | To et al. |
| 2011/0118601 A1 | 5/2011 | Barnes et al. |
| 2011/0155599 A1 | 6/2011 | Yakel et al. |
| 2011/0201881 A1 | 8/2011 | Emch |
| 2012/0029542 A1 | 2/2012 | Huang |
| 2012/0029543 A1 | 2/2012 | Lee |
| 2012/0116398 A1 | 5/2012 | Goldfarb et al. |
| 2012/0191116 A1 | 7/2012 | Flynn et al. |
| 2012/0198703 A1 | 8/2012 | Ranieri et al. |
| 2012/0203220 A1 | 8/2012 | Brannan et al. |
| 2012/0289987 A1 | 11/2012 | Wilson et al. |
| 2012/0303018 A1 | 11/2012 | Ladtkow et al. |
| 2013/0046233 A1 | 2/2013 | Green |
| 2013/0066149 A1 | 3/2013 | Mirza et al. |
| 2013/0144318 A1 | 6/2013 | Dinis Carmo |
| 2013/0165962 A1 | 6/2013 | Porshinsky et al. |
| 2013/0172895 A1 | 7/2013 | Wallace et al. |
| 2013/0197553 A1 | 8/2013 | Ng et al. |
| 2013/0211201 A1 | 8/2013 | Wongsiri |
| 2013/0289596 A1 | 10/2013 | Guo |
| 2013/0345515 A1 | 12/2013 | Fitzmaurice |
| 2014/0012076 A1 | 1/2014 | Mirza et al. |
| 2014/0031621 A1 | 1/2014 | Liu |
| 2014/0039533 A1 | 2/2014 | Palmer et al. |
| 2014/0054356 A1 | 2/2014 | Hartwick et al. |
| 2014/0066709 A1 | 3/2014 | Mirza et al. |
| 2014/0066964 A1* | 3/2014 | Mirza ............. A61B 17/32002 606/170 |
| 2014/0121456 A1 | 5/2014 | Mccormack et al. |
| 2014/0180282 A1 | 6/2014 | Brecheen et al. |
| 2014/0212456 A1 | 7/2014 | Vazquez-Cintron et al. |
| 2014/0276741 A1 | 9/2014 | Mckay |
| 2014/0276790 A1 | 9/2014 | Raybin et al. |
| 2014/0343357 A1 | 11/2014 | Mirza et al. |
| 2014/0371526 A1 | 12/2014 | Mirza et al. |
| 2015/0045822 A1 | 2/2015 | Mirza et al. |
| 2015/0073461 A1 | 3/2015 | Mccormack et al. |
| 2015/0080878 A1 | 3/2015 | Feng et al. |
| 2015/0080905 A1 | 3/2015 | Begemann et al. |
| 2015/0133982 A1 | 5/2015 | Park |
| 2015/0182248 A1 | 7/2015 | Palmer et al. |
| 2015/0196743 A1 | 7/2015 | Diederich et al. |
| 2015/0201959 A1 | 7/2015 | Guo |
| 2015/0265818 A1 | 9/2015 | Piskun et al. |
| 2015/0282832 A1 | 10/2015 | Mirza et al. |
| 2015/0320436 A1 | 11/2015 | Agee et al. |
| 2016/0081710 A1 | 3/2016 | Barnes et al. |
| 2016/0157880 A1 | 6/2016 | Aklog et al. |
| 2016/0235431 A1 | 8/2016 | Brown et al. |
| 2017/0042565 A1 | 2/2017 | Ellsworth et al. |
| 2017/0086803 A1 | 3/2017 | Nakanishi et al. |
| 2017/0105792 A1 | 4/2017 | Barnes et al. |
| 2017/0143364 A1 | 5/2017 | Mirza et al. |
| 2019/0262024 A1 | 8/2019 | Barnes et al. |
| 2019/0343546 A1 | 11/2019 | Brown et al. |
| 2020/0078039 A1 | 3/2020 | Mirza et al. |
| 2020/0107850 A1 | 4/2020 | Mirza et al. |
| 2020/0197039 A1 | 6/2020 | Hatch |
| 2021/0077139 A1 | 3/2021 | Mirza et al. |
| 2021/0369293 A1 | 12/2021 | Moungondo |
| 2022/0022909 A1 | 1/2022 | Lins et al. |
| 2022/0346819 A1 | 11/2022 | Barnes et al. |
| 2022/0354527 A1 | 11/2022 | Barnes |

FOREIGN PATENT DOCUMENTS

| | | |
|---|---|---|
| WO | 2007016141 A2 | 2/2007 |
| WO | 2012089767 A1 | 7/2012 |
| WO | 2013155472 A1 | 10/2013 |
| WO | 2014118752 A2 | 8/2014 |
| WO | 2014176206 A2 | 10/2014 |
| WO | 2014176206 A3 | 1/2015 |
| WO | 2020146458 A1 | 7/2020 |
| WO | 2020243412 A1 | 12/2020 |
| WO | 2020247476 A1 | 12/2020 |

OTHER PUBLICATIONS

Extended European Search Report for EP Application No. 20814659.7 dated Jun. 15, 2023.

* cited by examiner

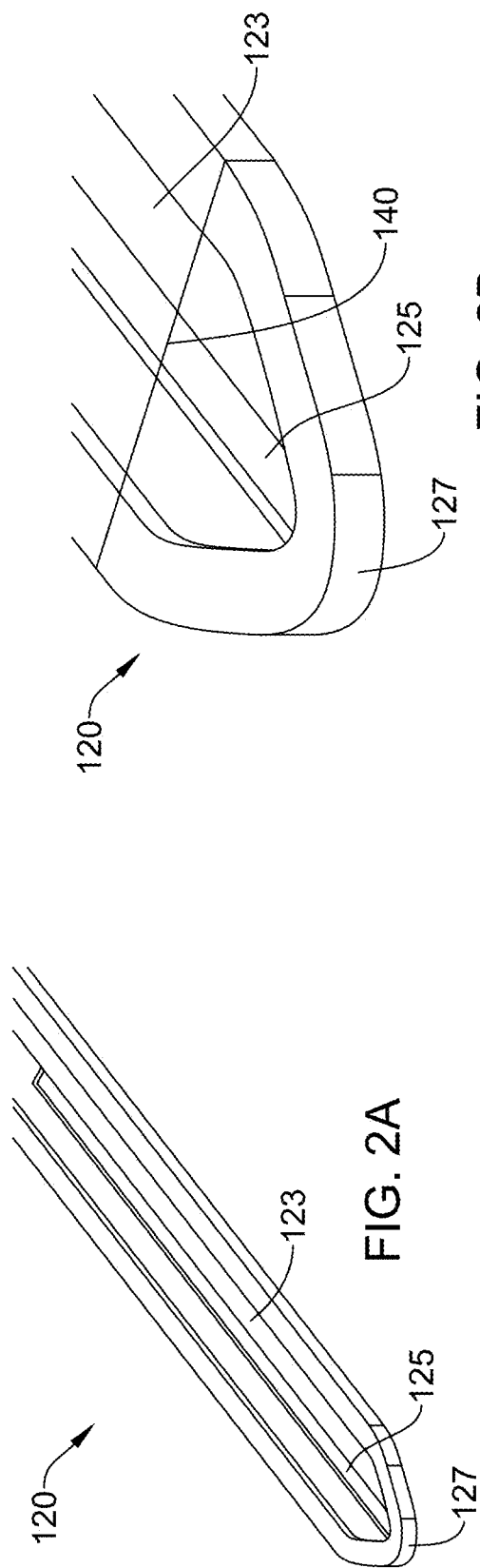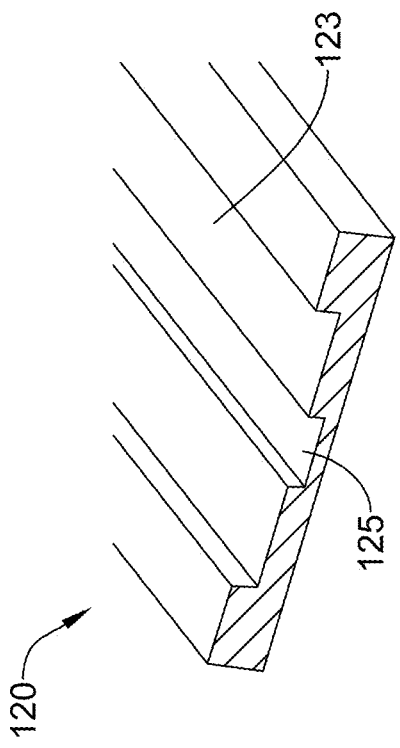

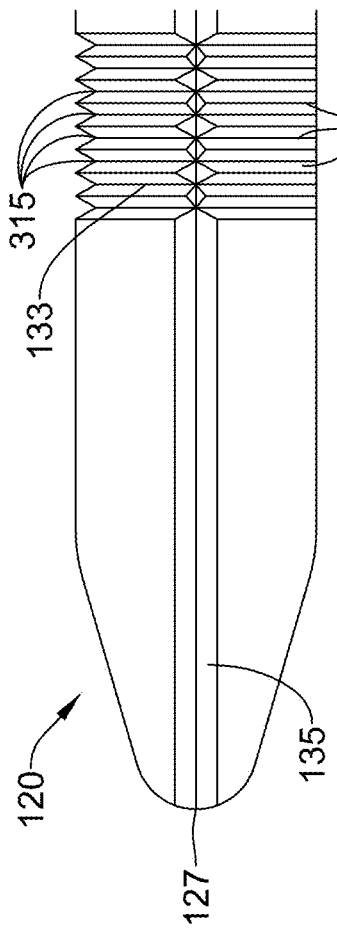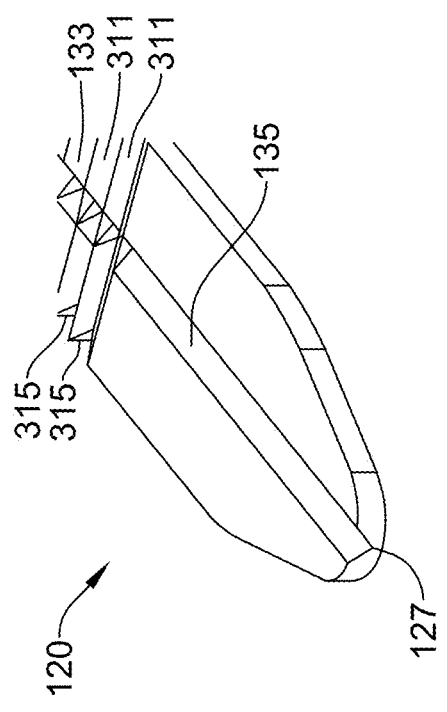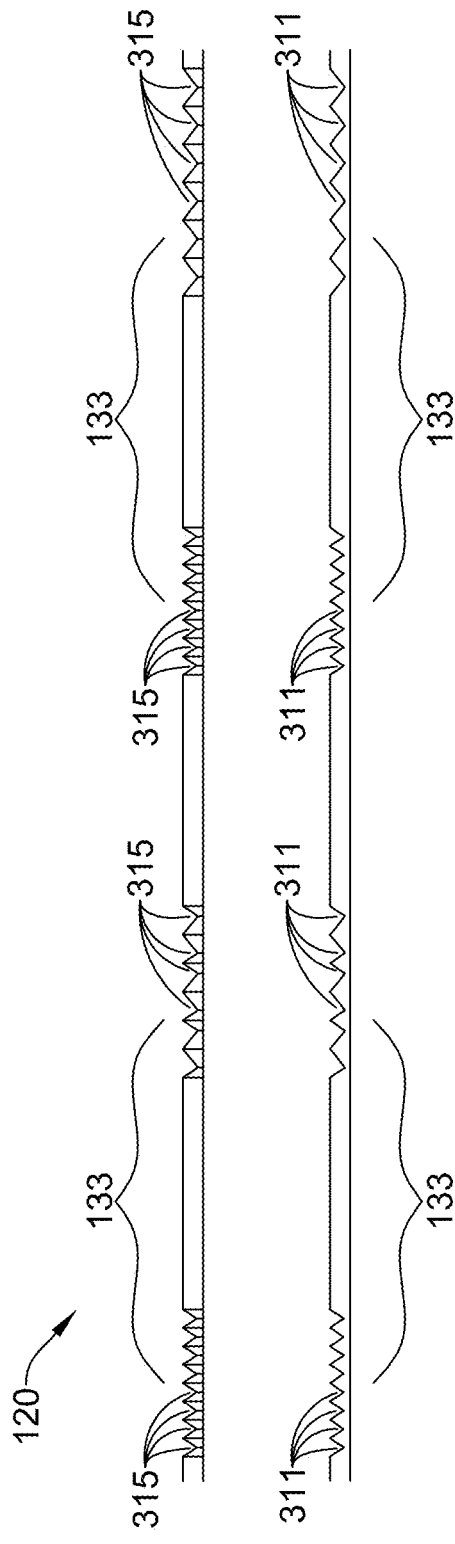
FIG. 3A
FIG. 3B
FIG. 3C

CUTTING DEVICE FOR TRIGGER FINGER AND OTHER SOFT TISSUES

CROSS REFERENCE TO RELATED APPLICATIONS

This application claims the benefit of U.S. Provisional Patent Application No. 63/182,259, filed Apr. 30, 2021 and U.S. Provisional Patent Application No. 63/231,029, filed Aug. 9, 2021 and U.S. Provisional Patent Application No. 63/232,863, filed Aug. 13, 2021 and is a Continuation in part of U.S. Design application Ser. No. 29/803,594, filed Aug. 13, 2021, the disclosures of which are incorporated herein by reference in their entirety for any and all purposes.

TECHNICAL FIELD

The present application is related generally to medical devices and methods. More specifically, the present application is directed to a surgical device for cutting soft tissue in the hand and potentially other parts of the body.

BACKGROUND

As minimally invasive surgery has evolved, numerous tools have been developed to treat medical conditions that have previously been treated with more invasive, open surgical techniques. Treatment of trigger finger is one such example. The first annular ("A1") pulley is a small band of tissue on the palmar side of a person's hand. (See FIG. 7.) In some cases, the flexor tendon in a finger thickens, and a nodule on the tendon can get caught on the A1 pulley and cause irritation. The flexor tendon can then become locked in place when a person flexes his or her fingers. This condition is commonly referred to as "trigger finger." To treat trigger finger, the A1 pulley is typically cut, to release the tendon, while leaving the A2-A5 pulleys intact.

Carpal Tunnel Syndrome (CTS) is another example of a common hand/wrist condition that causes pain, weakness, numbness, and tingling in the hand and arm. CTS occurs when the median nerve is compressed by the surrounding tissue. Severe cases of CTS may be treated with a surgical technique, carpal tunnel release (CTR), where the transverse carpal ligament is cut to relieve pressure on the median nerve.

One type of minimally invasive (or "less invasive") approach to treating trigger finger and CTS involves advancing a surgical blade through a small incision on the patient's wrist or palm and cutting the problematic tissue with the blade. Advancing a surgical blade through the patient's wrist, however, carries a risk of cutting non-target tissues and causing unwanted neurovascular injuries. Nerves, such as the median nerve or the ulnar nerve, and vascular structures, such as the superficial palmar arch, are just a few examples of tissues that may be accidentally damaged, potentially resulting in temporary or permanent nerve damage and paralysis. Damage to the tendons surrounding the surgical site, including bowstringing, lacerations and partial lacerations may also occur.

With minimally invasive surgical techniques for addressing trigger finger and CTS, the incision is typically so small that the blade is advanced to the treatment site with minimal or no visualization, thus increasing the risk of unwanted tissue damage. To try to make such techniques safer, some currently available devices use a hook blade, which is advanced in a horizontal position to avoid cutting and then turned to a more vertical orientation to hook and cut target tissue. Although some of these devices work well for cutting, they typically still require some type of introducer device to ensure safe advancement of the blade to the target tissue site. The introducer devices can often be bulky, awkward to use or overly complex.

Therefore, it would be advantageous to have improved soft tissue cutting devices for treating trigger finger and carpal tunnel syndrome. Ideally, such improved devices may also be used or adapted for use in other orthopedic procedures and/or surgical procedures in other parts of the body.

BRIEF SUMMARY

The present disclosure describes various examples of a device and method for treating trigger finger in a hand and/or cutting one or more soft tissues in other parts of the hand or body. The devices and methods typically include an introducer and a blade. In some cases, the introducer and blade may be separate devices, while in others they are included in one device. The method is performed minimally invasively (or "less invasively") than currently available techniques and may be performed with ultrasound visualization to facilitate the procedure.

In one aspect of the present disclosure, an introducer is provided for advancing a cutting device into a patient and below a target tissue. The introducer includes a handle and a shaft extending from the handle and having a flat shape with a guiding channel for guiding the cutting device along the shaft and below the target tissue. Optionally, the introducer may also include at least one ultrasound invisible region on the shaft, where each ultrasound invisible region includes multiple grooves in a top surface and/or a bottom surface of the shaft.

The device may also include a rotating channel within the guiding channel and deeper than the guiding channel. The rotating channel is configured for receiving an edge of the cutting device in a rotated configuration. In some embodiments, the introducer includes the cutting device, which is removably attached to the handle of the introducer. For example, the handle of the introducer may be attached to the cutting device by at least one break point, such that rotating the cutting device relative to the handle of introducer breaks the cutting device off the introducer at the at least one break point. Optionally, the introducer may also include a longitudinal groove disposed along at least a portion of the shaft, on a side of the shaft that is opposite the guiding channel. The shaft of the device may be curved in an upward direction facing an upper surface of the handle. In some embodiments, a distal end of the shaft forms a blade configured to cut soft tissue. Alternatively, the distal end of the shaft may be blunt or rounded. In some embodiments, the introducer is made of, or coated with, an echogenic material. In some embodiments, the handle of the introducer includes one or more grip-enhancing features.

In another aspect of the present disclosure, a method of cutting soft tissue in a hand of a patient may involve: advancing a shaft of an introducer into the patient's hand so that a distal end of the shaft is located beyond an A1 pulley in a finger of the hand; advancing a blade along the shaft to position a cutting surface of the blade beyond the A1 pulley; rotating the blade to position the cutting surface in a cutting orientation; retracting the blade proximally to cause the cutting surface to cut the A1 pulley; and removing the introducer and the blade from the patient's hand. The method may further involve using an ultrasound device to confirm a location of the shaft of the introducer in the patient's hand. Again, in some embodiments, the introducer and the blade are separate devices, while in others they are combined in one device.

In another aspect of the present disclosure, a method of cutting soft tissue in a patient may involve: advancing an introducer shaft into the patient to position a distal end of the introducer shaft beyond a target soft tissue; advancing a blade along a guiding channel on an upper surface of the introducer shaft, to position a distal end of the blade at or near the distal end of the introducer shaft; rotating the blade to rotate a cutting surface of the blade to an orientation at or near perpendicular relative to the upper surface of the introducer shaft; retracting the blade along the introducer shaft to cut the target soft tissue; and removing the introducer shaft and the blade from the patient.

In some embodiments, the introducer shaft and the blade are part of a soft tissue cutting device that also includes a handle attached to a proximal end of the introducer shaft and a slider rotatably attached to the handle and the blade. In such embodiments, advancing, rotating, and retracting the blade involves advancing, rotating, and retracting the slider, relative to the handle. Optionally, the method may also include rotating the slider to position the blade in an inactive position, before removing the introducer shaft and the blade from the patient. The method may also optionally include unlocking the slider from a locked position on the handle before advancing the introducer shaft into the patient. In some embodiments, the target soft tissue is an A1 pulley in a finger of a hand of the patient.

In another aspect of the present disclosure, a device for cutting soft tissue in a patient includes: a handle; an introducer shaft extending from the handle and comprising; a guiding channel; a rotating channel; and a rounded distal end; a blade; and a slider rotatably attached to the handle and the blade. The slider is configured to rotate relative to an upper surface of the handle and slide along the handle to advance and retract the blade along the introducer shaft. The handle may include multiple contoured areas for placement of a user's fingers while holding the handle. The introducer shaft may be flat and may have an upward curve. The blade includes a curved, proximally facing cutting surface. The slider is attached to the handle via a hinge and the device also includes a track along which the slider slides.

These and other aspects and embodiments are described in further detail below, in reference to the attached drawing figures.

BRIEF DESCRIPTION OF THE DRAWINGS

FIG. 2A is a top, perspective view of a shaft of the a soft tissue cutting device introducer of FIG. 1A, illustrating a guiding channel and a rotating channel;

FIG. 2B is an enlarged, top perspective view of a distal end of the shaft of FIG. 2A;

FIG. 2C is a cross-sectional, perspective view of the distal end of the shaft of FIG. 2B, with the sectional view defined by line 140 on FIG. 2B;

FIG. 3A is an enlarged, bottom perspective view of a distal end of a shaft of the introducer of FIG. 1B, illustrating an ultrasound invisible region and a central groove;

FIG. 3B is a bottom view of the distal end of the shaft of FIG. 3A;

FIG. 3C includes a side view (top panel) and a cross-sectional side view (bottom panel) of the shaft edge of the introducer of FIG. 1B, having four ultrasound invisible regions;

DETAILED DESCRIPTION

Figure 1A:
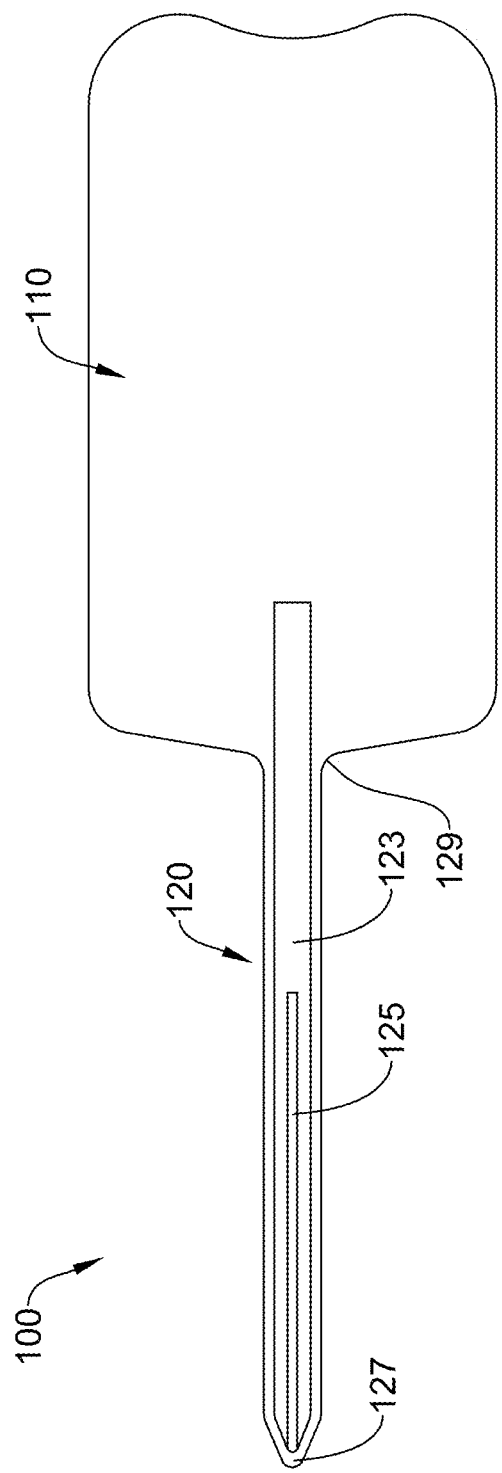
FIG. 1A is a top view of a soft tissue cutting device introducer, according to one embodiment.

This application is directed to a soft tissue cutting device and method, as well as an introducer for a soft tissue cutting device. Some embodiments of the soft tissue cutting device include a blade for cutting and an introducer for helping guide the blade to and from the anatomical location of the target soft tissue to be cut. Other embodiments include only an introducer, which is used with a separate blade. The introducer serves at least several main functions: to guide the cutting blade to a treatment site, the guide the cutting blade during cutting, and to shield the blade from non-target tissue on the opposite side of the introducer.

Embodiments described herein are specifically designed for cutting soft tissues in the human hand, most notably but not exclusively the A1 pulley (or other pulley(s)) in the fingers to treat trigger finger. These embodiments may also be used or modified for use, however, to cut other soft tissues in the hand, such as for a carpal tunnel release procedure, or in other anatomical locations, such as but not limited to the ankle, foot, elbow, shoulder or other joints. For example, various embodiments may be used to cut soft tissues in or near other joints to treat other nerve impingement syndromes. Therefore, although this disclosure focuses on treatment of trigger finger, the invention should not be interpreted as being limited to only that application.

The cutting device and introducer device disclosed herein are designed, respectively, for cutting soft tissue and guiding soft tissue cutting devices to a surgical site. In certain embodiments, the soft tissue cutting device is a pulley cutting device for treating trigger finger in the hand. In some cases, the pulley is an A1 pulley of a finger, and the soft tissue cutting device is a trigger release device that cuts the A1 pulley. While each finger has several pulleys, the A1 pulley is the pulley that is most often involved in trigger finger. The A1 pulley is an annular ligament of the finger that sits near the head of the metacarpal bone and lies in the flexor groove in the deep transverse metacarpal ligament. The A1 pulley, together with other annular pulleys and cruciate pulleys, governs the flexor mechanism of the hand and wrist. The A1 pulley provides biomechanical support to the underlying metacarpophalangeal joint and maintains joint stability and flexor tendon alignment. In a patient with trigger finger, the A1 pulley becomes inflamed or thickened, making it harder for the flexor tendon to glide through it as the finger bends. Over time, the flexor tendon may also become inflamed and develop a small nodule on its surface. When the finger flexes and the nodule passes through the pulley, there is a sensation of catching or locking. This condition, known as trigger finger or stenosing tenosynovitis, can be accompanied by pain or stiffness. The trigger release procedure involves cutting (or "releasing") the A1 pulley to enable the flexor tendon to glide freely.

In alternative embodiments, the soft tissue cutting device is a transverse carpal ligament cutting device that cuts a transverse carpal ligament in a carpal tunnel region. As described above, a CTR procedure involves cutting a transverse carpal ligament, to reduce median nerve compression and carpal tunnel pressures in the carpal tunnel region.

While the following descriptions are believed to be complete, the embodiments described are examples only. Any given embodiment may include features and/or components of other described embodiments or may be altered or adapted for alternative uses, without departing from the scope of the invention.

In this application, the term "distal" generally means "close to or in a direction toward target tissue," and the term "proximal" generally means "farther from or in a direction away from the target tissue." In other words, proximal and distal are relative terms. For example, when a user holds a treatment device and inserts one end of the treatment device into a patient to perform a treatment, the end of the device that is inserted into the patient will be referred to as the "distal end" of the device. The end of the device being held by the physician will be referred to as the "proximal end" of the device. Although these terms will be used consistently in this application, they should not be interpreted as limiting.

The present application describes a soft tissue cutting device that includes a blade and an introducer device configured to guide the blade to a target tissue and to guide the blade as it cuts. As mentioned above, in some embodiments, the introducer alone might be provided, for use with a separately available blade. In some embodiments, the soft tissue cutting device includes an introducer and a cutting blade that rotates relative to the introducer. In some embodiments, the introducer facilitates introducing a tissue cutting device having a first blade and a rotatable second blade into and through a patient's skin. The first blade surrounds and protects the rotatable second blade. In alternative embodiments, only one blade, the rotatable blade, is used. In some embodiments, a device includes a second blade that is protected by the introducer until the second blade is deployed for a cutting procedure. In various embodiments, the cutting device and the introducer are minimally invasive and can be used in a trigger finger release procedure, a carpal tunnel release procedure, or both.

Figure 1B:
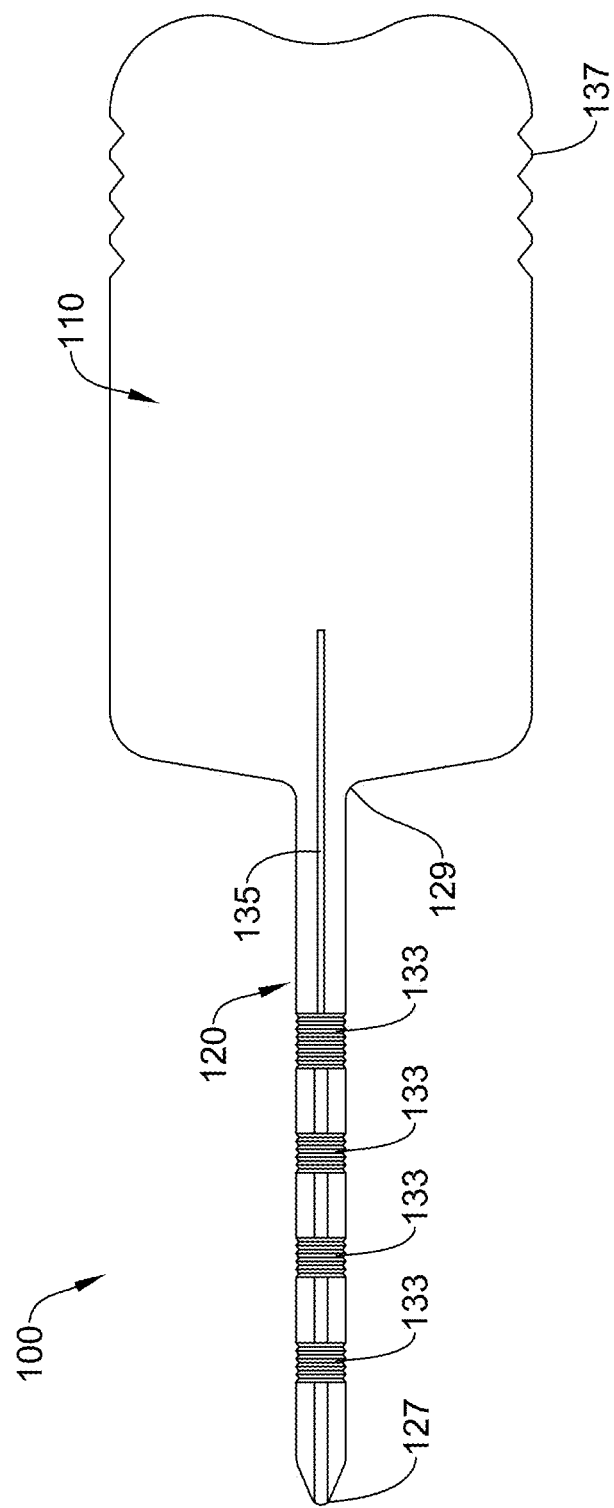
FIG. 1B is a bottom view of the introducer of FIG. 1B.

Referring to FIGS. 1A-1B, one embodiment of an introducer 100 (or "introducer device") is illustrated. FIG. 1A is a top view of the introducer 100, and FIG. 1B is a bottom view. Cutting devices that may be used with the introducer 100 will be described further below, but in general the introducer 100 may be used with any small, minimally invasive, or less invasive bladed device or cutting device that is sized and shaped to be compatible with it. The introducer 100 and a cutting device can be used to cut any desired soft tissue structure in the body of a human or animal subject, such as but not limited to an A1 pulley or other pulley in a finger, the transverse carpal ligament, other ligaments, tendons, fascia, nerves, cartilage, and/or any other soft tissue. Although this disclosure focuses on the examples of trigger finger and CTS treatment, the introducer 100 may be used or adapted for use in any other suitable tissue cutting procedure.

As shown in FIGS. 1A-1B, in some embodiments, the introducer 100 may include a handle 110 and a shaft 120. The shaft 120 extends from a shaft base 129 to a shaft distal end 127. The introducer 100 may be approximately the same thickness along its length or may have varying thicknesses at different regions along the introducer 100. The shaft 120 may have a shape (e.g., rounded, flat, etc.), dimensions, and profile (straight, curved, inclined, etc.) configured to address the location and properties of an intended surgical site and/or tissue, such as an A1 pulley in a finger.

Figure 5:
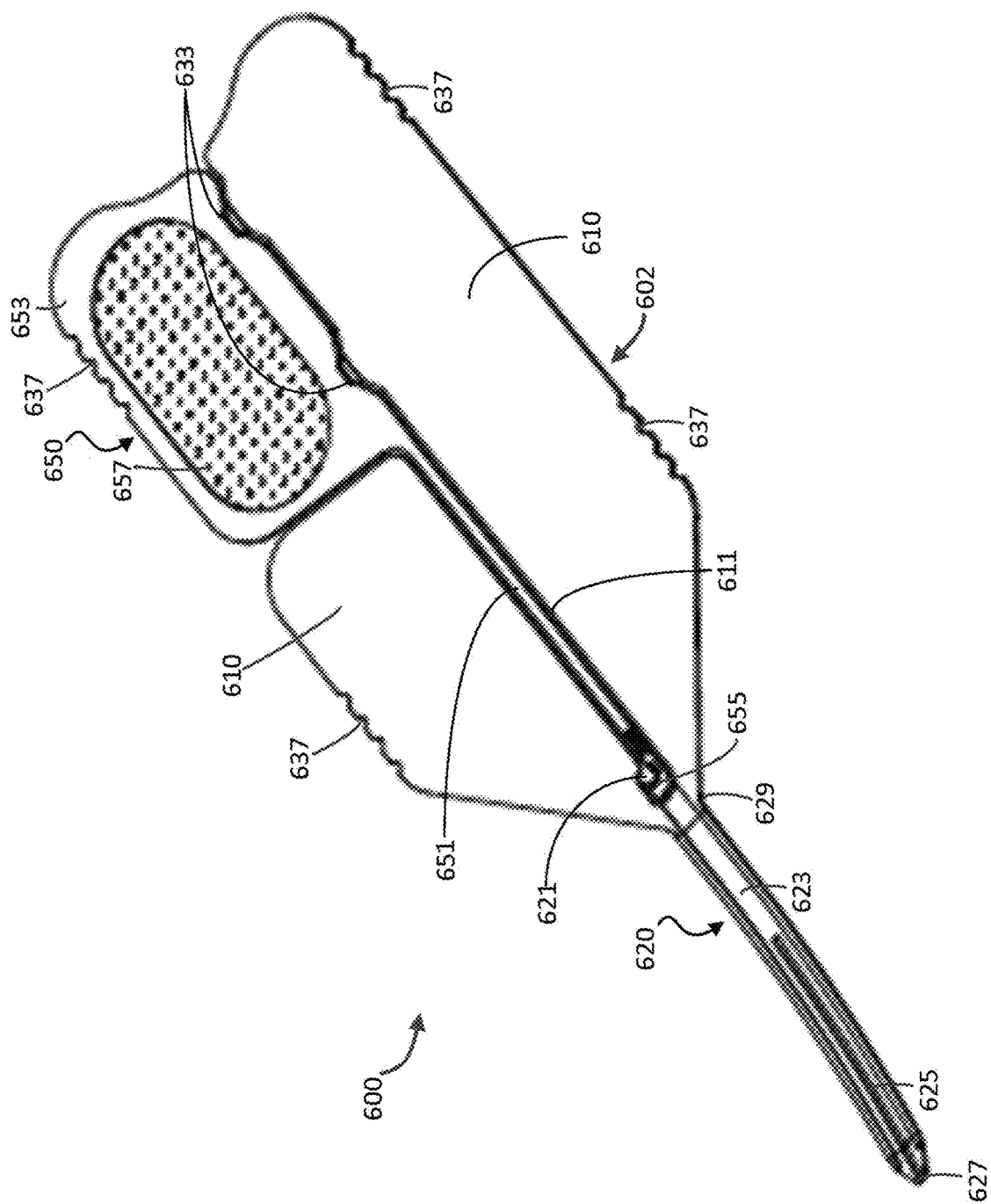
FIG. 5 is a perspective view of a soft tissue cutting device with introducer, according to one embodiment.

For example, the shaft 120 of the introducer 100 for use in cutting an A1 pulley may have an upward curve (as shown in the embodiment of FIG. 5). In some embodiments, the thickness of the introducer 100 may be about 0.005 inch to about 0.025 inch. In some embodiments, the shaft 120 of the introducer 100 may have a width of about 0.05 inch to about 0.25 inch and a length, measured from the shaft distal end 127 to the shaft base 129, of about 1.0 inch to about 2.0 inches.

Referring now to FIGS. 1A and 2A-2C, an upper surface of the introducer 100 may include a guiding channel 123 and a rotating channel 125. The guiding channel 123 may be an indent or trough formed in the introducer 100, having a shape and dimensions (depth and/or thickness) configured to allow at least a portion of a soft tissue cutting device to fit within the guiding channel 123, such that the guiding channel 123 can provide a passage and serve as a guide for introducing a cutting blade to the surgical site. The guiding channel 123 is also configured to prevent exposure of the cutting blade (or blades) of the soft tissue cutting device, to prevent injury to nerves and/or other tissues during introduction of the soft tissue cutting device and/or during the surgical procedure. The guiding channel 123 may extend from a point on the handle 110 beyond the shaft base 129 and along the length of the shaft 120 to a point at or near the distal end 127 of the shaft 120.

The shape and dimensions of the guiding channel 123 are designed to accommodate the cutting blade(s) that will be used with the introducer 100. In various embodiments, the width of the guiding channel 123 may be about 0.05 inch to about 0.25 inch, and the depth of the guiding channel 123 may be about 0.0001 to about 0.025 inch.

The rotating channel 125 is formed as an indent or trough in the guiding channel 123 and is deeper than the guiding channel 123. The rotating channel 125 is configured to allow at least a portion of the cutting blade(s) to rotate while being housed within the guiding channel 123, without exposing the cutting blade(s) to surrounding tissues and to position the cutting blade(s) in an appropriate cutting position without injury to surrounding tissues. The rotating channel 125 may extend from a point at or near the distal end 127 of the shaft 120 to a point between the distal end 127 of the shaft 120 and the shaft base 129. Alternatively, the rotating channel 125 may extend the entire length of the guiding channel 123. The rotating channel 125 may allow the cutting blade(s) to rotate to any desired angle between 0 degrees and 180 degrees and to be locked in various configurations depending on the desired application. For example, the allowed angle of rotation may be about 45 degrees to about 135 degrees, or in some embodiments about 75 degrees to about 105 degrees, or more specifically about 90 degrees.

The shape, dimensions, and/or position of the rotating channel 125 within the guiding channel 123 may be selected for a specific soft tissue cutting device and intended procedural use. For example, in certain embodiments, the width of the rotating channel 125 may be about 0.005 inch to about 0.025 inch, and the depth of the rotating channel may be about 0.0001 to about 0.025 inch.

As seen in FIGS. 1A, 1B, 2A and 2B, the shaft 120 is tapered to form the shaft distal end 127 (or "shaft distal tip") in the shape of a rounded point. In alternative embodiments, the shaft distal end 127 may be blunt or may have a blade configured to cut soft tissue. Although the shaft distal end 127 may alternatively have other shapes, the rounded tip may be advantageous for passing through tissue. It may be important to provide the shaft distal end 127 with a rounded shape that is configured to allow the shaft distal end 127 to move easily through tissue without being so sharp/pointed as to risk unwanted damage/cutting as it is advanced, for example by passing through the tendon sheath while accessing the A1 pulley in a trigger finger repair procedure. The shaft distal end 127 may thus have a radius of curvature selected to be not so large as to make advancement through tissue difficult but not so small as to risk accidental tissue cutting/damage. In some embodiments, for example, the radius of curvature of the shaft distal end 127 is between about 0.020 inch and about 0.050 inch, or ideally about 0.030 inch.

Referring now to FIGS. 1B and 3A-3C, in some embodiments, the shaft 120 of the introducer 100 may optionally include one or more regions 133 that are differentially reflective with respect to ultrasound. These regions 133 may be included on any surface (e.g., top, bottom, sides) or combination of surfaces of the shaft 120. In some embodiments, these regions 133 include elements that increase reflectivity, while in other embodiments, such as those illustrated in FIGS. 1B and 3A-3C, the regions 133 include elements that intentionally reduce reflectivity. Regions 133 of reduced reflectivity may be included, for example, on a component that is inherently highly reflective, such as a flat stainless-steel surface. In this example, the regions 133 of reduced reflectivity are visible under ultrasound when compared to the highly reflective adjacent surface of the component itself.

Certain device components (e.g., cutting blades) may be manufactured in a manner (e.g., using specific materials, designs etc.) that creates suboptimal ultrasound images or artifacts that interfere with visualization and therefore may not be suitable for ultrasound guided procedures. For example, as previously stated, a highly reflective surface (e.g., flat stainless steel) may create a very bright image accompanied by artifact, both of which reduce overall visualization. As such, regions 133 of differential reflectivity can be used for identification of device components and/or general measurement, position or orientation. One example would be the inclusion of one or more regions in the introducer 100 that do not reflect ultrasound waves. The regions 133 of reduced reflectivity appear darker relative to the bright, highly reflective surface of the introducer 100 that is immediately adjacent each of the regions 133. These "dark" regions 133 of reduced echogenicity can be used for identification of device components and/or general measurement, position, or orientation during ultrasound guided procedures. As another example, "dark" regions 133 of reduced echogenicity may be placed on shaft 120 and used in conjunction with the cutting blade to provide relative depth of the cutting blade within the surgical site. In this example, these "dark" regions 133 may be spaced at known intervals (e.g., about 2 mm to about 4 mm apart), to provide a user with a "scale" from which to discern the relative size and/or distance of a target tissue to be cut during advancement of the cutting blade within the guiding channel 123. The user may visually identify these evenly spaced ultrasound invisible regions 133 as dark regions with images of the surgical blade between them. This may assist the user in assessing a relative distance from the cutting edge to a tissue of interest inside the patient's body. In some embodiments, the textured markings may be used to determine when a cutting blade is appropriately positioned for rotation. Although these examples discuss regions of reduced reflectivity, regions of increased reflectivity may be used for the same purposes. Furthermore, in alternative embodiments, a device component may include regions of reduced reflectivity and other regions of increased reflectivity, for the purposes of component identification and/or general measurement, position, or orientation.

Referring again to FIGS. 3A-3C, the ultrasound invisible regions 133 may be configured to be undetectable by ultrasound by inclusion of multiple grooves having shapes and dimensions that internally reflect ultrasound waves, so the ultrasound waves are not reflected back to a sensor. Ultrasound invisible regions 133 may include planar grooves 311, which may be oriented in any direction along the plane of the shaft 120, and perpendicular grooves 315, which may be perpendicular and/or otherwise angled relative to the planar grooves 311, along the thickness of the shaft 120. In embodiments having ultrasound invisible regions 133 with multiple planar grooves 311 and perpendicular grooves 315, the planar grooves 311 and perpendicular grooves 315 may be approximately adjacent. Planar grooves 311 and perpendicular grooves 315 of the ultrasound invisible regions 133 may be perpendicular to the length of the shaft 120. The width and depth of the planar grooves 311 and perpendicular grooves 315 may be of any size and shape that would be undetectable by ultrasound, for example during ultrasound-guided surgery. The planar grooves 311 and perpendicular grooves 315 within a single ultrasound invisible region 133 may have differing widths and depths, as depicted in the two leftmost ultrasound invisible regions 133 in FIG. 3C. In embodiments with multiple ultrasound invisible regions 133, each ultrasound invisible region 133 may have planar grooves 311 with different widths and depths, as depicted in the two rightmost ultrasound invisible regions 133 in FIG. 3C.

By way of example, in various embodiments, a perpendicular groove 315 may have a width of about 0.005 inch to about 0.060 inch and a depth of about 0.005 inch to about 0.060 inch. In one specific embodiment, the shaft 120 may have one or more sets of wider perpendicular grooves 315 and one or more sets of narrower perpendicular grooves 315. A wider perpendicular groove 315 may have a width of about 0.034 inch, and a narrower perpendicular groove 315 may have a width of about 0.020 inch. Both of these types of grooves 315 may have a depth of about 0.010 inch. Each perpendicular groove 315 is configured to have sides that generate a reflective angle for sound waves (e.g., ultrasound waves) that hit them. In various embodiments, for example, the sides of each perpendicular groove 315 are angled to deflect the ultrasound signal at an angle of about 11 degrees or greater. In one specific embodiment, an angle of reflectance off a side of one of the perpendicular grooves 315 may be about 22 degrees. Different perpendicular grooves 315 may have different shapes, either in the same embodiment or in different embodiments, such as V-shaped, U-shaped, a combination of curved and straight sides, or the like. The perpendicular grooves 315, the planar grooves 311, and any other grooves or surface features may be formed into the shaft 120 by any suitable manufacturing process, such as but not limited to electrochemical etching, machining, electro-discharge machining (EDM), stamping, coining, or broaching.

Referring again to FIGS. 1A and 1B, in some embodiments, the introducer 100 includes a handle 110 extending proximally from the shaft 120. The handle 110 may have any suitable size and shape and may be made from the same piece of material the shaft 120 is made from, so that the introducer 100 is a monolithic, one-piece device. Alternatively, the handle 110 may be made from different types of material (e.g., metal or plastic) than shaft material, may be a separate piece from the handle, and/or may be multiple pieces. In some embodiments, as illustrated in FIG. 1B, handle 110 may include a textured grip 137 on one or both sides. The top and/or bottom surfaces of the handle 110 may also include a texture.

The bottom surface of the introducer 100 (FIG. 1B) may optionally include a central groove 135 that extends centrally and parallel to the length of the shaft 120 from a point at or near the shaft distal end 127 to a point on the handle 110 beyond the shaft base 129. The central groove 135 may be of any size and shape that would be detectable by ultrasound (i.e., echogenic), for example during ultrasound-guided surgery. Alternatively, the central groove 135 may be a triangular-shaped valley, having two sides that meet at a single point. According to various embodiments, the central groove 135 may have a width of about 0.005 inch to about 0.025 inch, and a depth of about 0.005 inch to about 0.025 inch.

In some embodiments, the shaft 120 may be tapered to form a pointed profile at the shaft distal end 127. In alternative embodiments, the shaft distal end 127 may be blunt or may have a blade configured to cut soft tissue.

The introducer 100, as discussed above, may advantageously be used as a guide for introduction of a soft tissue cutting device, including a hooked blade configured for cutting an A1 pulley using a retroactive action. For example, the introducer 100 may first be inserted and positioned appropriately within a surgical site, such as by advancing through the subject's skin adjacent a desired tissue plane (e.g., the tissue plane may be such that the tissue to be cut is positioned above the introducer 100). However, the exact positioning of the introducer 100 will depend on the configuration of the soft tissue cutting device to be used, as well as on the type of cutting procedure to be performed. Thereafter, at least a portion of the soft tissue cutting device (e.g., a hook shaped cutting blade) may be advanced within the guiding channel 123 and rotated after reaching a desired depth, such that the hooked shaped cutting blade is positioned behind and below the tissue to be cut. The soft tissue cutting device may then be elevated and/or retracted in a proximal direction (e.g., within the guiding channel 123 or slightly over it) to cut the tissue in a desired manner. In various embodiments, ultrasound invisible regions 133 on the shaft 120 may be used to provide information relating to the progress of the soft tissue cutting device being advanced within the guiding channel 123, and/or when the soft tissue cutting device is appropriately positioned. The introducer 100 may be pulled out upon positioning of the soft tissue cutting device in the surgical site and before the surgical procedure, and/or may be left in place during the surgical procedure.

Various embodiments of the introducer 100 may be made of any medically and/or surgically suitable material and may be flexible or inflexible, depending on its particular use. The introducer 100 may be made of a 420 stainless steel or any other material that is appropriate for surgical use. In some embodiments, the material may be echogenic.

The features of FIGS. 1A-B, 2 and 3A-3C are provided by way of example, and any of the features found on one side in the depicted embodiments may be found on other sides in other example embodiments.

Figure 4B:
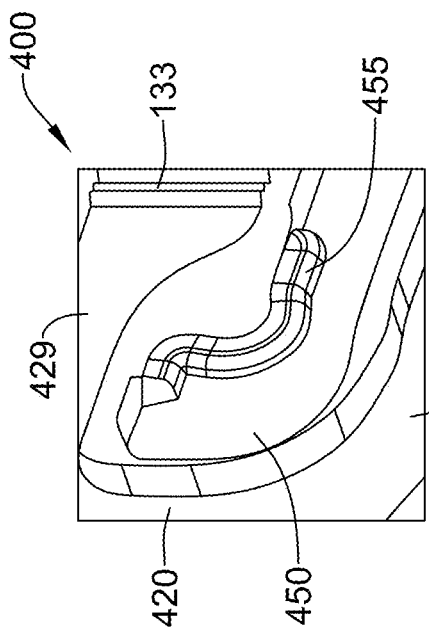
FIG. 4B is a perspective view of the second blade of the cutting device of FIG. 5A.
Figure 4D:
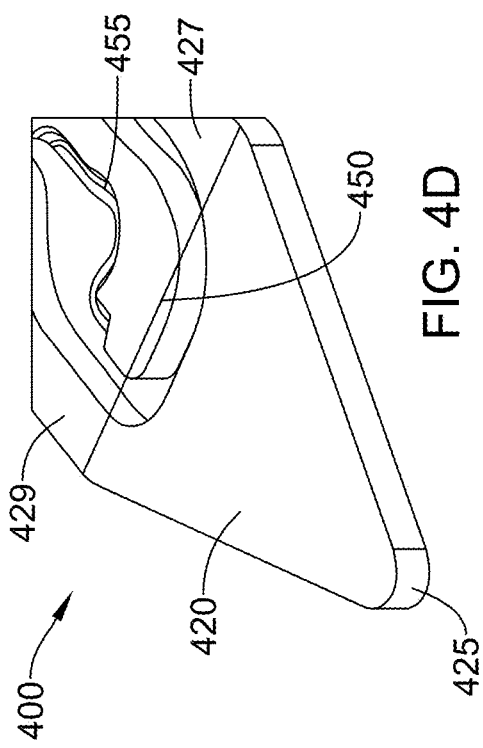
FIG. 4D is a perspective view of the distal portion of the cutting device of FIG. 5A.
Figure 4A:
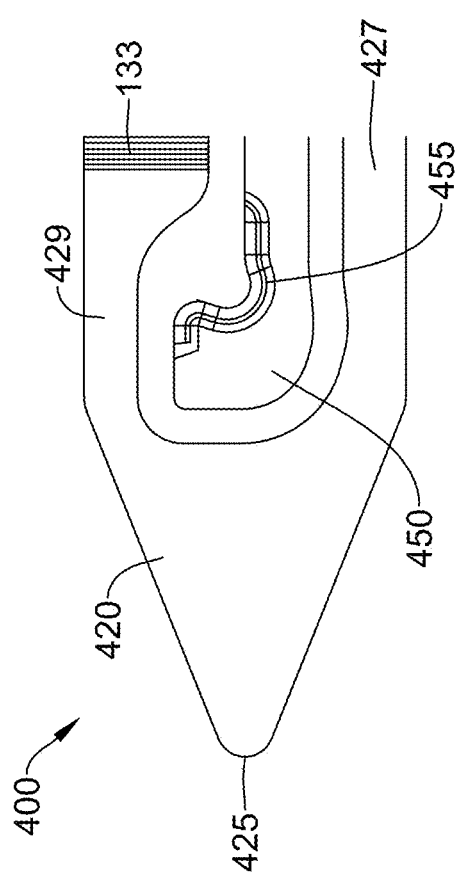
FIG. 4A is a top view of a distal portion of a cutting device having a first blade and a second blade, according to one embodiment.
Figure 4C:
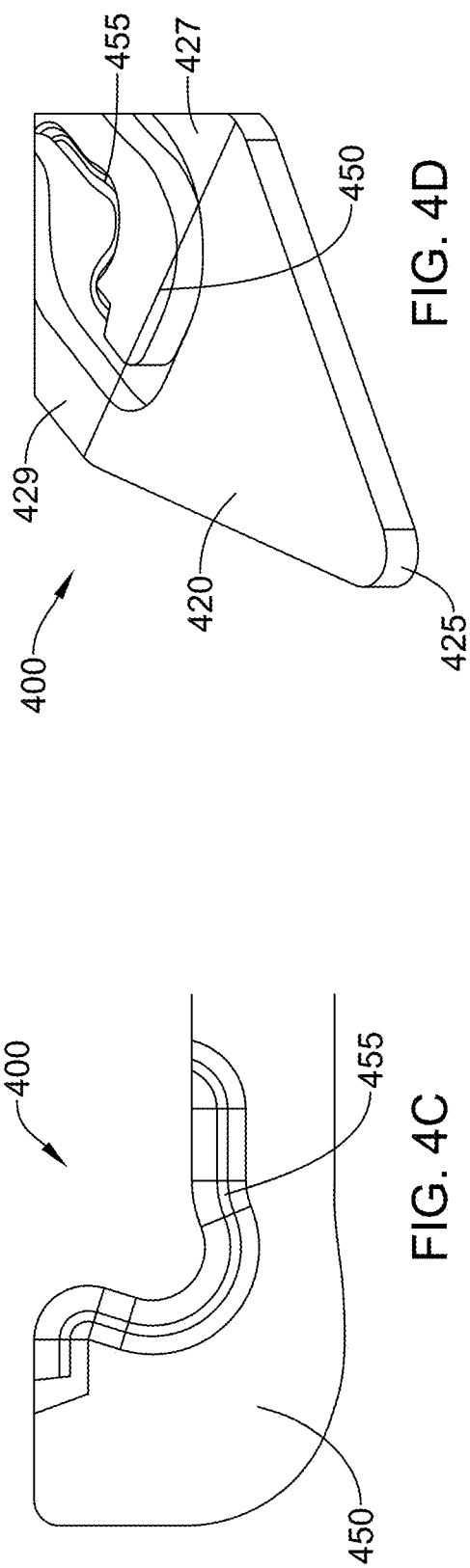
FIG. 4C is atop view of the distal portion of the second blade of the cutting device of FIG. 5A.

Referring now to FIGS. 4A-4D, a distal end of a cutting blade device 400 is illustrated in top view (FIG. 4A), perspective views (FIGS. 4B and 4D), and second-blade-only top view (FIG. 4C). In some embodiments, the cutting blade device 400, which may be used with the introducer 100, includes a first blade 420 and a second blade 450 that collectively define a blade assembly. The first blade 420 may be coupled to the second blade 450. The first blade 420 is an exposed blade. As used in the present disclosure, "exposed blade" refers to a blade that is not protected from contact with tissue (when introduced without an introducer device). In contrast, "unexposed blade" refers to a blade that is protected from contacting tissue by another structure of the device 400 (when introduced without an introducer device). Advantageously, the second blade 450 is rotatable relative to the first blade 420, such that the second blade 450 is configured to rotate between a first (inactive) position and a second (active) position. The second blade 450 is in the same plane as the first blade 420 when the second blade 450 is in the first position. This arrangement of the tissue cutting device provides a low-profile design that enables the tissue cutting device to be inserted into tight spaces underneath a patient's skin, adjacent a desired tissue region. Additionally, the cutting device may be configured to engage with an introducer 100 by, for example, inserting into the guiding channel 123 of the introducer 100.

The second blade 450 may be rotated into a different plane from the first blade 420 as the second blade 450 is rotated from the first position toward the second position. When the second blade 450 is in the first (inactive) position, the second blade 450 is an unexposed blade that is protected (at least in part) by the first blade 420. The second blade 450 can remain in the first position until needed for a cutting procedure. Then, when it is desired to cut tissue using the second blade 450, the second blade 450 is rotated into the second (active) position, thereby becoming an exposed blade.

The second blade 450 can have any desired degree of rotation as needed to suit a particular cutting procedure. In some instances, the second blade 450 may be configured to rotate in a range of between 0 degrees and 180 degrees. In other cases, the second blade 450 may be configured to rotate in a range of between 0 degrees and 90 degrees.

The first blade 420 may be configured to facilitate introduction of the tissue cutting device 400 through the dermis and into subcutaneous tissue of a patient. In some embodiments, the tissue cutting device has both the first blade 420 to introduce the device into the skin, and the second blade 450 that can be unexposed and protected until needed to cut or release the tissue of interest. In an alternative embodiment, the first blade 420 may be blunt, so the cutting device may be inserted without cutting tissue. The cutting device may also be configured to be inserted after the introducer 100 has been inserted.

The first blade 420 has a distal end 425. In some cases, the outer surface of the first blade 420 includes one or more cutting surfaces. In other cases, the distal end 425 of the first blade 420 defines a tip not intended for cutting tissue. For example, in certain cases, the distal end 425 defines a blunt tip (e.g., a rounded, convex end) not intended for cutting tissue. In other cases, the distal end 425 defines a sharp-edged tip intended for cutting tissue. For example, in some cases, the distal end 425 defines a dissecting tip or a cutting tip. In various embodiments, the distal end 425 of the first blade 420 may include a pointed tip, a curved edge, a straight edge of uniform length, an angled surface that is longer on one side than on the other, or any other desired configuration. In addition, the one or more cutting surfaces of the first blade 420 (where provided) can extend along the entire outer surface of the first blade 420, along a major length of the outer surface of the first blade 420 (i.e., along a length that is greater than 50% of a length of the outer surface), or along only a minor portion of the outer surface of the first blade 420, such as only at the distal end 425.

The second blade 450 may also have at least one cutting surface 455. In some embodiments, the cutting surface 455 of the second blade 450 is less sharp than the cutting surface and/or distal end 425 of the first blade 420. In other cases, the cutting surface 455 of the second blade 450 is sharper than some (or all) of the outer surface of the first blade 420. In other cases, the cutting surface 455 of the second blade 450 has the same sharpness as the outer surface (or as the cutting surface) of the first blade 420.

The cutting surface 455 can be a single cutting surface or one of many cutting surfaces. Also, the cutting surface 455 can be a curved surface, a straight surface (of uniform length), or an angled surface that is longer on one side than on the other side (e.g., a downward-angled cutting surface). In addition, the cutting surface 455 can face toward or away from the second blade handle (not pictured) or can face toward either side of the cutting blade device 400. In some cases, the cutting surface 455 is provided on an interior surface of the second blade 450. In other cases, the cutting surface 455 is provided on an outer surface of the second blade 450 (e.g., to provide a superficial cutting surface). In certain embodiments, the cutting surface 455 of the second blade 450 is a retrograde cutting surface configured to facilitate cutting of tissue when the second blade 450 is moved in a retrograde manner. In other cases, the cutting surface 455 of the second blade 450 is an antegrade cutting surface configured to facilitate cutting of tissue when the second blade 450 is moved in an antegrade manner. In yet other cases, the cutting surface 455 is both a retrograde and antegrade cutting surface. The examples identified herein are not limiting, and any type of cutting surface can be used as cutting surface 455.

In various embodiments, example disclosed components of the cutting blade device 400 may exhibit echogenic properties due to being coated in an echogenic coating and/or having an echogenic structure, including an etching and/or a textured surface. In any embodiment of the present disclosure, the second blade 450 is optionally echogenic. In embodiments of this nature, the second blade 450 can have a flat superficial surface, etching, or an echogenic coating, with each of these features being designed to improve visualization of the second blade 450 under ultrasound. The first blade 420 and second blade 450 may additionally have at least one textured surface, such as the regions 133 described above.

The cutting blade device 400 further includes a first arm 427 and a second arm 429. The first arm 427 and the second arm 429 define opposite sides of the first blade 420. The first arm 427 is coupled to and extends between the first blade 420 and a first blade handle (not shown). The second arm 429 is coupled to the first blade 420 and extends from the first blade 420 toward a second blade handle (not shown).

Figure 6:
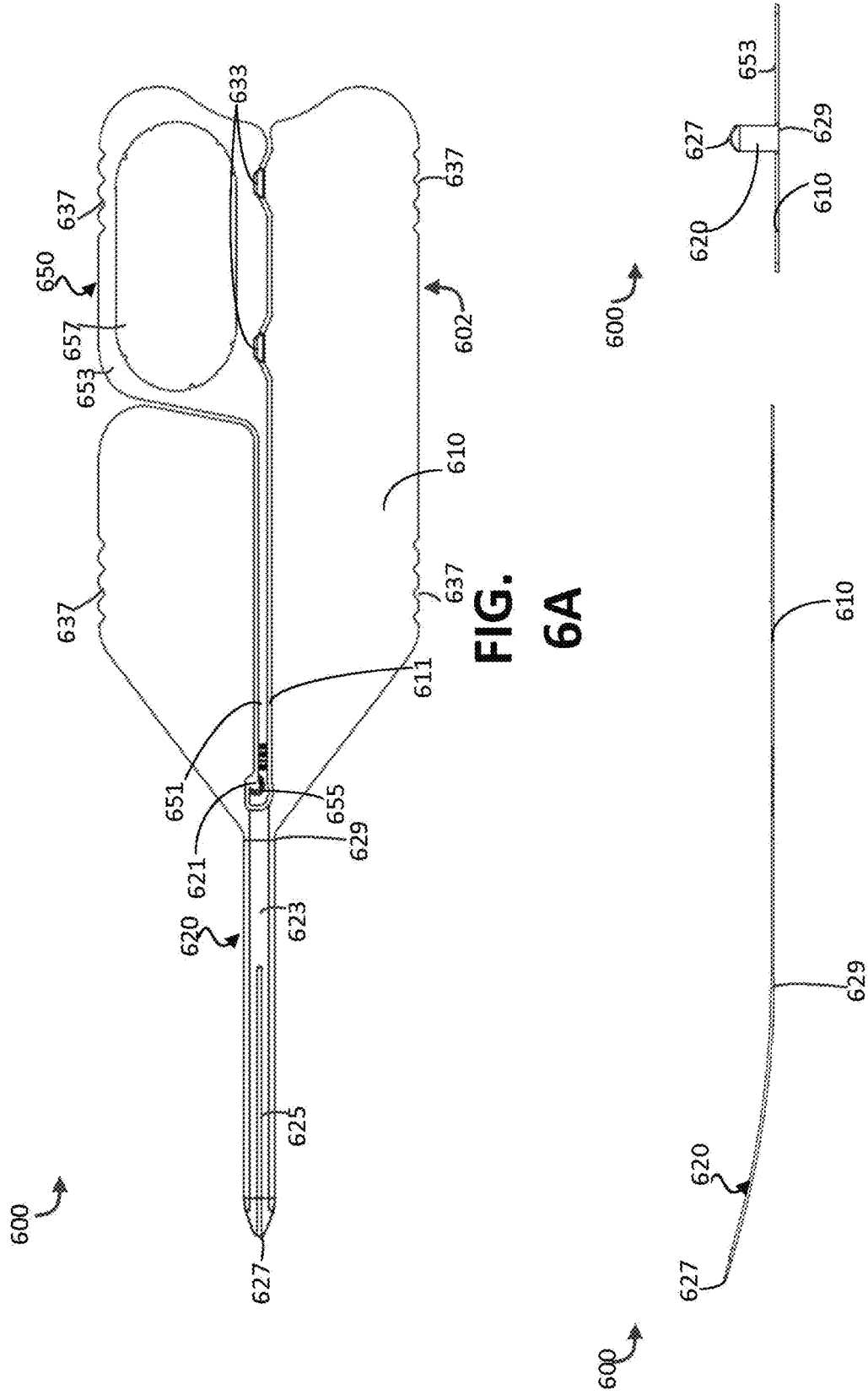
FIGS. 6A-6C are top, side and rear views, respectively, of the soft tissue cutting device of FIG. 5.

Referring now to FIGS. 5 and 6A-7C, another embodiment of a soft tissue cutting device 600 (or simply "cutting device 600") is illustrated. In this embodiment, the cutting device 600 includes an introducer portion 602 and a blade portion 650, which are removably attached to each other via multiple break points 633. The introducer portion 602 includes an introducer handle 610 and a shaft 620. The introducer handle 610 may optionally include surface features 637, which may help with gripping the cutting device 600. The shaft 620 may include a guiding channel 623, a rotation channel 625, a distal end 627, and a proximal end 629. The blade portion 650 includes a blade handle 653 with an optional textured surface 657 and a cutting blade 651 with a cutting edge 655. The cutting device 600 is configured such that the blade portion 650 is removably coupled to, and nested within, the introducer handle 610 for storage and before use, as illustrated in FIGS. 5 and 6A. The blade handle 653 may be attached to the introducer handle 610 via one or more break points 633. The introducer handle 610 may optionally include a longitudinal channel 611, in which the cutting blade 651 rests before use, and a blade opening 621 at the end of the longitudinal channel 611 close to the shaft proximal end 629. The blade opening 621 provides a housing in which the distal portion of the blade portion 650, including the cutting surface 655, can nest.

The cutting device 600 may have any suitable dimensions and be made of any suitable materials, such as but not limited to stainless steel, other biocompatible metals, or any suitable biocompatible plastics or polymers. In one embodiment, for example, a maximum width of the cutting device 600 may be about 1.442 inches, a width of the introducer shaft 20 may be about 0.140 inches, a length of the cutting device may be about 4.720 inches, and a length of the introducer handle 610 may be about 3.096 inches. In various embodiments, however, the maximum width of the cutting device 600 may range from about 0.5 inch to about 4 inches, a width of the introducer shaft 20 may range from about 0.05 inch to about 0.3 inch, a length of the cutting device may range from about 3 inches to about 6 inches, and a length of the introducer handle 610 may range from about 2 inches to about 5 inches.

The blade portion 650 may include any of the features described above. The introducer portion 602 may include any of the features described for the introducer 100 above and may be used similarly for guiding the cutting blade 651 to a surgical site. For example, upon appropriate positioning of the shaft 620 within the surgical site, the blade portion 650 may be decoupled from the handle 610 of the introducer portion 602 (e.g., by twisting or otherwise moving the blade portion 650 to disrupt the break point 633). The surgical blade 651 may then be guided to the surgical site using the guiding channel 623 and thereafter turned to rest within the rotation channel 625, before being retracted to cut the target tissue.

The shaft 620 of the introducer portion 602 may curve in a manner that is appropriate for a given procedure in which the soft tissue cutting device 600 may be used. For example, as shown in the side view of FIG. 6B, the shaft 620 of the introducer portion 602 may curve upward (toward the top surface of the cutting device 600) in some embodiments. The curve may have a radius of any length appropriate for a given procedure. In the embodiment shown, for example, the shaft 620 angles upward at approximately an 18-degree angle relative to the longitudinal axis of the rest of the cutting device 600. In other embodiments, the shaft 620 may be flat or angle upwards from between about 0 degrees and about 45 degrees. The guiding channel 623 of the introducer portion 602 may be configured to extend to the distal end 627 of the shaft 620. In some embodiments, the shaft distal end 627 may include a blade for cutting soft tissue.

The soft tissue cutting device 600 may be used to cut soft tissue (e.g., ligament, fascia, or tendon) of a patient in treating trigger finger or carpal tunnel syndrome, for example. Alternatively, the method may be used to cut any soft tissue structure in any suitable part of the body.

Generally, a method for using the soft tissue cutting device may involve: advancing the shaft 620 into a body region to position the distal end 627 at or near the target tissue; advancing the blade portion 650 along/within the guiding channel 623; rotating the cutting blade 651 from a first position to a second position, such that it fits within the rotation channel 625; and retracting the cutting blade 651 to cut the target tissue.

In some embodiments, the method includes applying anesthetic to the patient's skin. Thereafter, the shaft 620 of the introducer portion 602 is placed through and into the patient's skin adjacent a desired tissue plane. In some cases, the shaft 620 is placed deep to the desired tissue plane, such that the tissue to be cut is positioned above the shaft 620. The positioning of the shaft 620 will depend on the configuration of the blade portion 650, as well as on the type of cutting procedure to be performed.

In some embodiments, a small incision is made in the patient's skin. In some cases, this incision can be made by using the distal end 627 of the shaft 620—e.g., when the distal end 627 has a cutting edge. In other cases, where the shaft distal end 627 is blunt, a separate device (e.g., a scalpel) may be used to make the incision.

In some embodiments, the cutting blade 651 may be positioned within the guiding channel 623, when the shaft 620 is advanced through the patient's skin. In alternative embodiments, the blade portion 650 is removed from the handle 610 of the introducer portion 602 by severing at the break points 633 (e.g., by twisting). The cutting blade 651 of the blade portion 650 may then be advanced through the guiding channel 623 of the introducer portion 602, before the shaft 620 is inserted into the skin of the patient. Alternatively, the shaft 620 may be inserted into the patient, and the cutting blade 651 may then be advanced along the guiding channel 623 thereafter.

The introducer portion 602 may be placed into subcutaneous tissue of the patient, such that the outer surface of the shaft distal end 627 located in or near a desired tissue plane. Preferably, this placement is performed under ultrasound guidance, in some embodiments using regions 133 to detect the placement of the introducer portion 602. In embodiments where the blade portion 650 is inserted with the introducer portion 602, the cutting blade 651 remains in a first position (within the guiding channel 623) that does not expose the cutting edge of the cutting blade 651 during the insertion and initial placement of the introducer portion 602 into the patient's body. The cutting blade 651 is turned only after the introducer portion 602 is positioned as desired. In embodiments where the introducer portion 602 is inserted without a blade portion 650, the blade portion 650 is inserted into the guiding channel 623 of the introducer portion 602 after the introducer portion 602 is adjacent or proximate a desired tissue plane. In these embodiments, the blade portion 650 is inserted with the cutting blade 651 in a first position that does not expose the cutting edge 655 of the cutting blade 651. Then, the blade handle 653 can be rotated to cause the cutting blade to rotate from its first position toward its second position, to become an exposed blade for cutting. The cutting edge 655 is then used to cut the tissue in a customary manner. As discussed above, the manner of cutting may, vary depending on the type and location of the cutting edge 655. For example, the cutting blade 651 may need to be pushed or pulled to cut the tissue. Once the tissue is cut, the introducer portion 602 and the tissue blade portion 650 are pulled out of the incision to complete the surgical procedure. In some embodiments, the tissue cutting device 600 may be discarded after use.

Use of embodiments of the introducer portion 602 and tissue blade portion 650 may include steps in addition to those noted above. For example, when inserting the introducer portion 602, the handle 610 may help prevent the operator from inserting the cutting device 600 too far into the body region. An operator can apply rotational force to the blade portion 650 (for example, by rotating the cutting blade handle 653) to cause the one or more break points 633 to disrupt, thereby separating the blade portion 650 from the introducer portion 602. In certain embodiments, the operator can apply shear force (e.g., by pulling or pushing) the cutting blade handle 653 to cause the one or more break points 633 to disrupt. The operator can then freely move and rotate the blade portion 650 to perform cutting. After cutting, the operator can grasp and pull the introducer handle 610 and the blade handle 653 to remove the cutting device 600 from the body, or the blade portion 650 may be removed first.

In some cases, the method is a carpal tunnel release procedure for treating carpal tunnel syndrome. In such cases, the distal end the shaft 120 of the introducer portion 602 may be inserted at a location proximal to the transverse carpal ligament. From this location, the introducer portion 602 may be further placed deep to (i.e. below) the transverse carpal ligament and superior to (i.e., above) the flexor tendon group, such that the shaft distal end 627 of the introducer portion 602 is distal to the transverse carpal ligament (i.e., on the side of the ligament closest to the fingers), the shaft 620 is deep to the transverse carpal ligament, and the handle 610 is proximal to the transverse carpal ligament (i.e., on the side of the ligament closest to the elbow). The introducer portion 602 is initially flat (i.e., parallel to the patient's hand). When the introducer portion 602 is in this location, the blade portion 650 is inserted within the guiding channel 623 of the introducer portion 602. Thereafter, the cutting blade handle 653 may be rotated to rotate the cutting blade 651 from its first (horizontal, non-cutting) position toward its second (vertical, cutting) position. This rotation exposes the cutting blade 651 to the transverse carpal ligament. The cutting blade 651 is then used to cut the transverse carpal ligament, for example, by moving the cutting blade 651 distal to proximal against the transverse carpal ligament.

While the introducer portion 602 and tissue cutting devices 600 have been described as having blades, alternative cutting mechanisms can be used in alternative device embodiments. For example, in some embodiments, the cutting blade 651 may be replaced with an energy based cutting mechanism, such as but not limited to an energy delivery cutting mechanism that uses electricity, heat, monopolar or bipolar radiofrequency energy, ultrasound, laser, cryotherapy, or any other suitable energy delivery (or energy removal) device to cut soft tissue. Such energy-based tissue cutting devices may include any of the features described above, despite having a non-bladed cutting mechanism, and may generally be used in a similar manner.

In various alternative embodiments, an introducer portion of a soft tissue cutting device such as those described above may include additional or alternative features. For example, the introducer shaft may have slot to guide a device with a corresponding tool that attaches via the slot. In some embodiments, a handle mechanism may include a blade handle integrated with an introducer handle. This may facilitate moving the blade portion distally and proximally in the horizontal position and the vertical position. In some embodiments, the introducer shaft may include a fiber optic cable to transmit light, laser or other energy from the tip of the device to allow for image capture (picture/video) and/or for energy delivery to treat tissue. An energy source and electronics may be embedded in the handle, or the handle may include a connecter to connect to an outside energy source and/or electronics. In other embodiments, the introducer shaft may include a lumen or tube extending from the handle through the shaft to the tip of the device to transfer fluid to and/or from the tip of the device, for example irrigation fluid and/or suction. This conduit may also be used to sense a pressure gradient change from the tip to the base of the device. This may be helpful in determining procedure completeness. In some embodiments, the introducer may include a slot with a holder for tube or needle blade (e.g., a needle blade) that allows the cutting needle to be advanced along the introducer to cut the tissue plane. In some embodiments, the handle of the introducer may be configured to be connected to a surgical robot device.

Embodiments of the introducer portion 602 may vary in size and/or curvature, may be made of a variety of materials, including metal and plastic, may have variable transparency, and may have variable echogenicity, including special treatments to increase or decrease echogenicity. These features can be used for identifying device regions or components, measurement, location, and/or orientation. Areas of reduced echogenicity may be preferred against a background of highly reflective surfaces. Introducers can be paired with a sharp tip or blunt tip trocar or similar device that can be used during introduction and/or maneuvering of the introducer. In some embodiments, the introducer may be formed as tube, and the user slides the cutting device through the tube. Alternatively, the introducer may be a slotted tube, and the cutting device could be contained entirely within the slotted tube, or the slot can be used to guide the device through the tube. The tube slot may be of variable length and width. In other embodiments, the introducer may be curved but open. Wall contours can vary to facilitate control of the cutting device(s) moved over it. In some embodiments, the introducer may be primarily flat, but the lateral sides of the introducer are curved to create a central channel to help contain the cutting device(s). The cutting device(s) may be wholly or partially recessed within the introducer. The central channel may be of variable width and/or depth, and some embodiments may include multiple channels. Some embodiments may include combined channels to promote cutting device control, such that thinner channels are contained within wider channels.

In some embodiments, a guiding mechanism may be placed along the introducer, such that the cutting device(s) may pass through the guiding mechanism. The guiding mechanism controls the position and direction of the device(s) with respect to the introducer. For example, guiding mechanisms may include one or more enclosed circular channels, open semi-circular channels, guideposts along the length of the introducer, or magnets.

In method embodiments, following positioning of the cutting device, the operator manually rotates the device to expose the cutting blade. In flat introducer configurations, the cutting device is rotated from a position more parallel with the introducer to a position more perpendicular to the introducer, thus moving the blade from a less exposed position to a more exposed position. If the introducer is more circular and enclosed, or slotted, the cutting device is rotated to expose the cutting surface from within the introducer. The cutting device may be rotated manually using the handle of the cutting device. Optionally, an additional ergonomic handle may be attached to the cutting device to facilitate and control the rotation and subsequent cutting motion. As the cutting device is rotated, the cutting device may naturally fall into one or more of the control and guiding mechanisms previously described, such as the channels and guideposts. Features of the cutting device and introducer can facilitate this coupling through mechanical or other means.

There may be times when it is advantageous to introduce fluid along or through the introducer to perform hydrodissection or deliver anesthetics or other injectable substances. Traditional needles, blunt tipped cannulas or similar may be passed through or over the introducer to deliver injectable substances. The introducer may have one or more fully enclosed ports, through which needles, blunt tipped cannulas or similar may be passed to deliver fluids. When the introducer is fully enclosed or slotted, these ports may be contained on the outer surface of the introducer, the inner surface of the introducer, or both. When the introducer is flat, these ports may be placed anywhere along the surface of the introducer. When the introducer is flat and contains one or more channels as described above, traditional needles, blunt tipped cannulas, or similar may be passed within one or more these channels.

Figure 7:
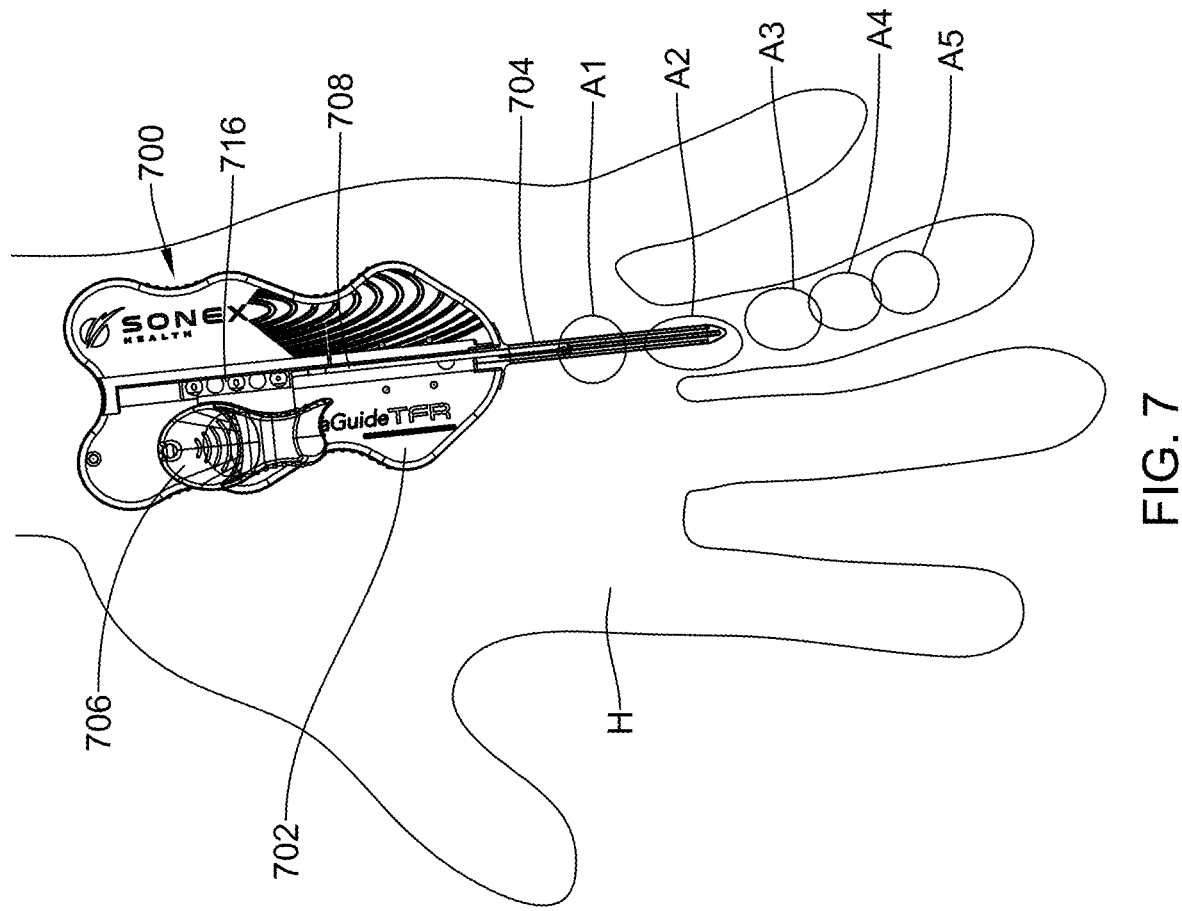
FIG. 7 is palmar view of a human hand with a soft tissue cutting device according to one embodiment positioned on the palm of the hand.

Referring now to FIG. 7, the palm side of a human hand H is illustrated, with the locations of the A1-A5 pulleys of the ring finger illustrated with circles. Overlying the image of the hand H is another embodiment of a soft tissue cutting device 700, which is explained in more detail below. This embodiment of the soft tissue cutting device 700 includes a handle 702, an introducer shaft 704 extending from the handle 702, and a slider 706 (or "blade handle") attached to a blade 708 and rotatably attached to the handle 702 via a hinge 716. The slider 706 advances, rotates, and retracts the blade 708, relative to the handle 702 and the introducer shaft 704, to cut targeted soft tissues, such as the A1 pulley to treat trigger finger. As mentioned above, although this embodiment of the soft tissue cutting device 700 is shown and described for use in trigger finger release procedures, it may alternatively be used (or adapted for use) in carpal tunnel release procedures and/or other soft tissue cutting procedures in other parts of the body.

With reference to FIGS. 8A-8D, the soft tissue cutting device 700 is illustrated in top view, perspective view, side view, and bottom view, respectively. These views show that the handle 702 (or "introducer handle") includes multiple side contoured areas 703 (or "finger holds") and a top surface contoured area 705, which make it easier for the user to hold the handle 702 and which help prevent the cutting device 700 from slipping in the hand. In this embodiment, the side contoured areas 703 and top surface contoured area 705 are made up of ridges and may also include additionally textured surfaces to further help prevent slippage. These contoured areas 703, 705 and textured surfaces are optional, and in alternative embodiments the handle 702 may have any suitable size, shape, and features.

Figure 8A:
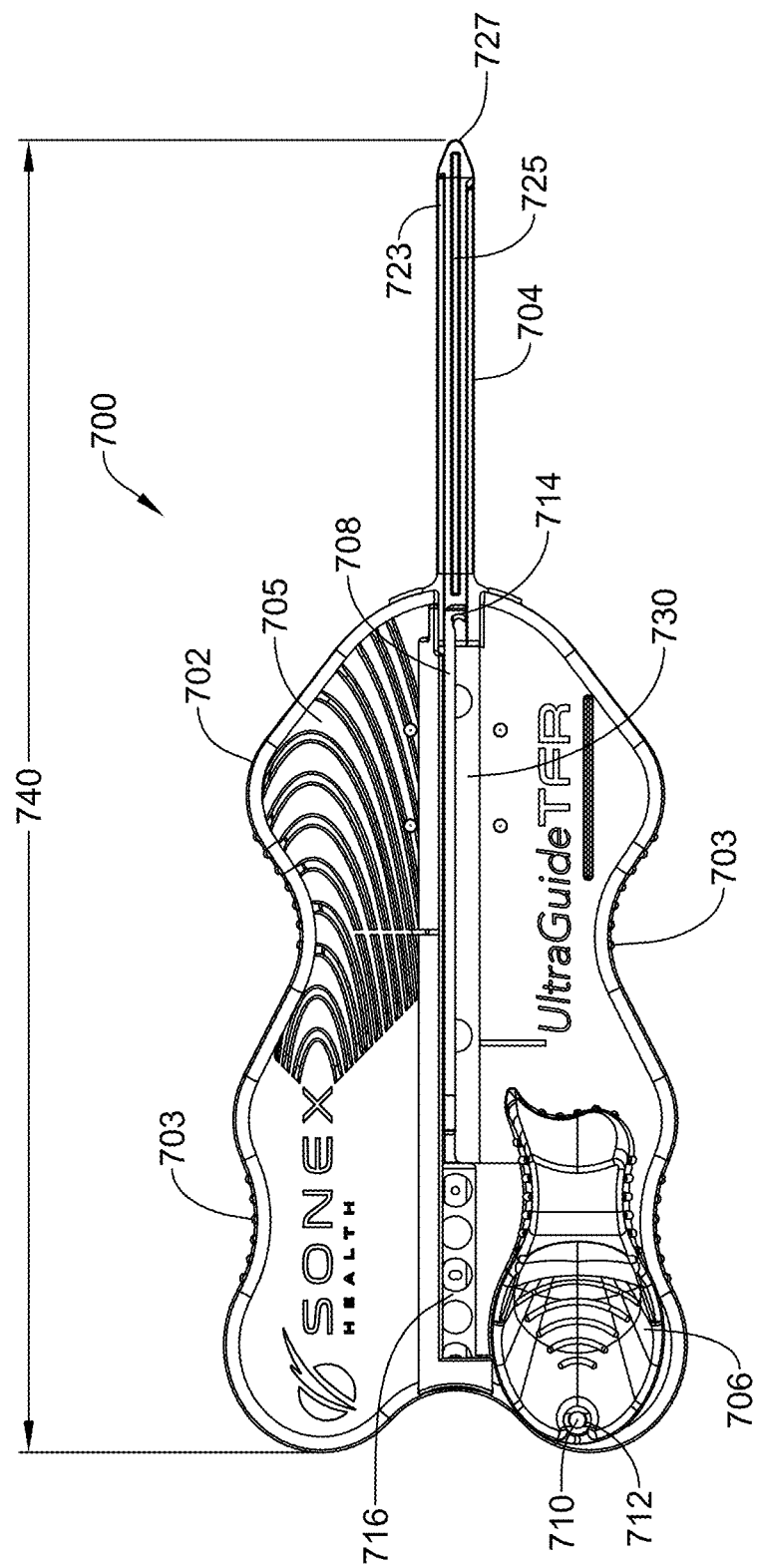
FIGS. 8A-8D are top, perspective, side and bottom views, respectively, of the soft tissue cutting device of FIG. 7.
Figure 8B:
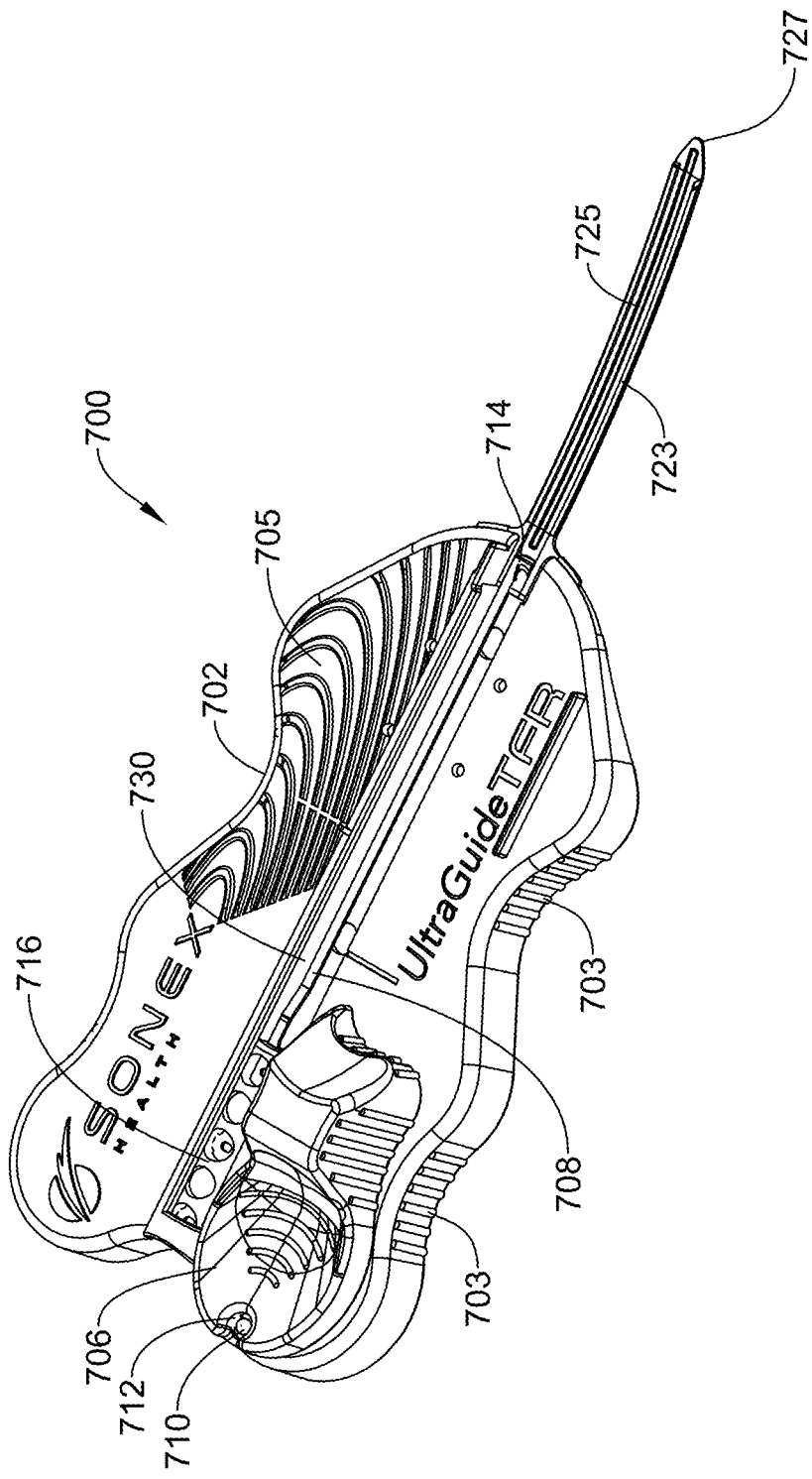
Figure 8C:
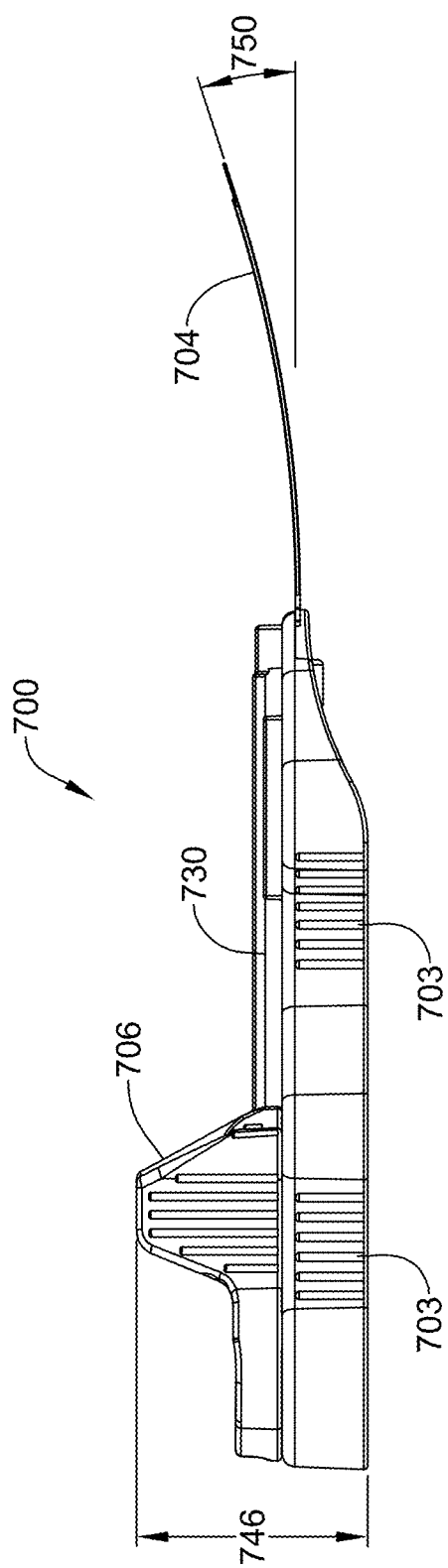

The soft tissue device 700 also includes an introducer shaft 704 attached to and extending from the handle 702, with an upward curve to facilitate advancement into the finger for accessing the A1 pulley. As seen in FIGS. 8A and 8B, the introducer shaft 704 includes a guiding channel 723, a rotating channel 725, and a curved distal end 727, as in the previously described embodiments. According to various embodiments, the introducer shaft 704 may include any (or all) of the features described above for the shaft 120 of the introducer 100, such as but not limited to the dimensions and shape of the shaft 120 and the dimensions, shapes, and features of the guiding channel 123, the rotating channel 125, the curved distal end 127 and the upward curve.

The soft tissue device 700 further includes a blade 708, which is attached to a slider 706 at its proximal end and has a cutting surface 714 near its distal end. In this embodiment, the cutting surface 714 faces proximally, and the distal end of the blade 708 is configured like a hook. The slider 706 is attached to the blade 708 via the hinge 716 (best seen in FIG. 8A) and includes an aperture 712 that fits over a locking feature 710 on the handle 702. When not in use, the slider 706 is locked in place relative to the handle 702 via the aperture 712 fitting over the locking feature 710. To operate the soft tissue cutting device 700, the user rotates the slider 706 (via the hinge 716) to raise the slider 706 off the locking feature 710, then moves the slider 706 forward and rotates it back onto the upper surface of the handle 702. In alternative embodiments, the aperture 712 and the locking feature 710 may be replaced by any other suitable mechanism for locking the slider 706 in place on the handle 702. Alternatively, the handle 702 might not include any locking feature for the slider 706. The purpose of the locking feature 710 and the aperture 712 is to secure the slider 706 in place while the soft tissue cutting device 700 is not in use or is being advanced into the patient, to prevent the slider 706 and thus the blade 708 from inadvertently sliding along the cutting device 700 and/or rotating up to activate the blade 708. Once unlocked, the slider 706 can be moved back and forth along a track 730 on the handle 702. Generally, the slider 706 is advanced distally to advance the blade 708, then rotated upward to activate the blade 708, then retracted proximally to cause the blade 708 to cut soft tissue. These steps are described in further detail below.

Figure 8D:
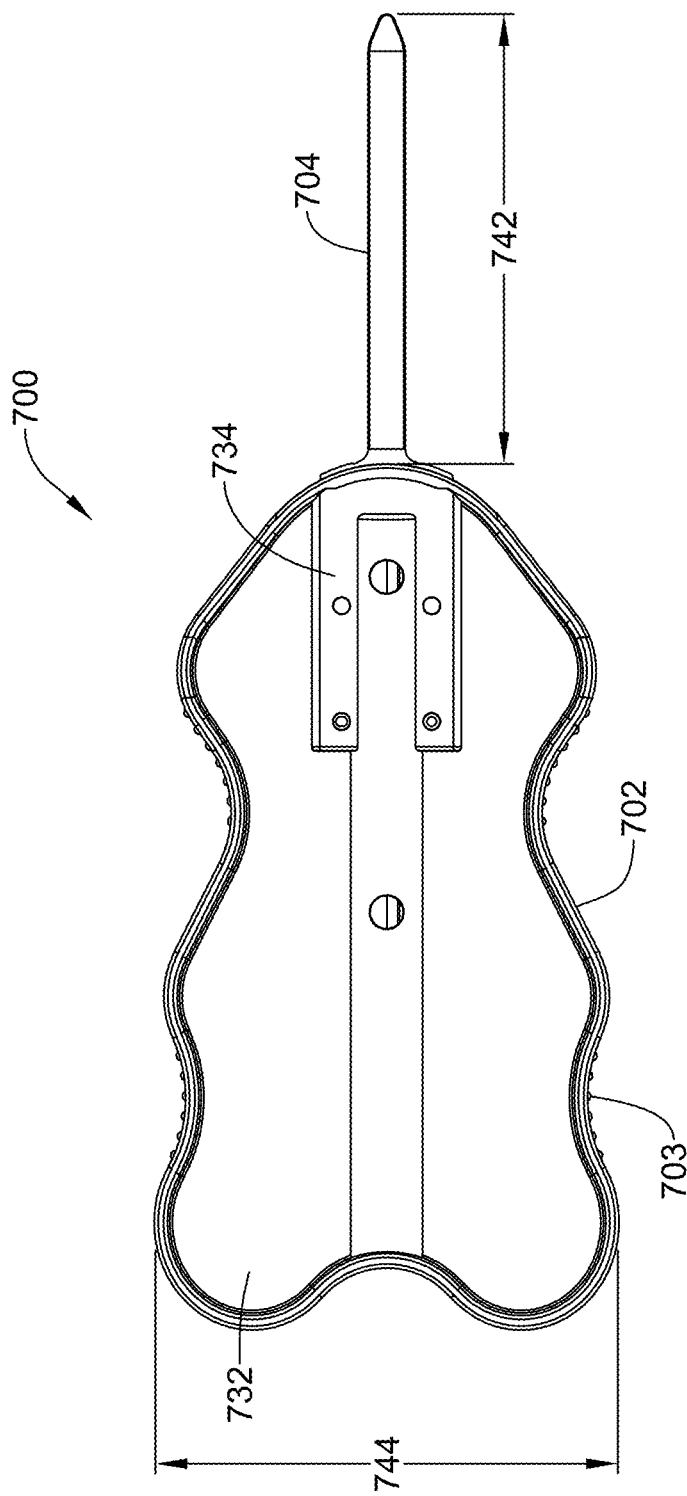

FIG. 8D is a bottom view of the soft tissue cutting device 700. This figure shows that the introducer shaft 704 is attached, in this embodiment, to an introducer support member 734, which is attached to the bottom of the handle 702. In this embodiment, the introducer shaft 704 and the introducer support member 734 are one piece of metal. The support member 734 may be glued, welded, fastened, or attached by any other suitable method to the handle 702. In alternative embodiments, the introducer shaft 704 may be attached to the handle 702 by any other suitable means, such as a differently shaped support member or any other suitable attachment mechanism.

In various embodiments, the soft tissue cutting device 700 and its components may have any suitable dimensions. For example, in some embodiments a total length 740 (FIG. 8A) of the soft tissue cutting device 700, from a proximal end of the handle 702 to the distal end 727 of the introducer shaft 704, may be from about 3 inches to about 8 inches, or in some cases from about 4 inches to about 6 inches, and in one embodiment about 4.964 inches. In some embodiments, a shaft length 742 (FIG. 8D) of the introducer shaft 704, may be from about 0.5 inch to about 5 inches, or in some cases from about 1 inch to about 3 inches, and in one embodiment about 1.643 inches. In some embodiments, a width 744 (FIG. 8D) of the handle 702 may be from about 1 inch to about 5 inches, or in some cases from about 1 inch to about 3 inches, and in one embodiment about 1.753 inches. In some embodiments, a height 746 (FIG. 8C) of the soft tissue cutting device 700, from the bottom surface of the handle 702 to a tallest point on the slider 706, may be from about 0.35 inch to about 3 inches, or in some cases from about 0.50 inch to about 2 inches, and in one embodiment about 0.88 inch. In some embodiments, the introducer shaft 704 may be angled upwards, toward the top surface of the handle 702. The amount of angle and the beginning of the curvature of the introducer shaft 704 may vary between various embodiments. The curvature may be measured as an angle 750 (FIG. 8C) in relation to a longitudinal axis 748 of the handle 702. For example, in some embodiments, the introducer shaft 704 may have a curvature that forms an angle 750 from about 1 degree to about 45 degrees, or in some cases from about 5 degrees to about 30 degrees, and in one embodiment about 18 degrees.

In various embodiments, the soft tissue cutting device 700 may be made of any suitable materials. For example, in one embodiment, the handle 702 and the slider 706 may be made of a plastic or polymer, and the blade 708 and the introducer shaft 704 may be made of stainless steel or any other suitable biocompatible metal. In other embodiments, all components of the soft tissue cutting device 700 may be made of the same material. In some embodiments, the soft tissue cutting device 700 is disposable after one use. Alternatively, the soft tissue cutting device may be made of material(s) that can be sterilized and may be reusable after sterilization. In various embodiments, the soft tissue cutting device 700 may be provided in multiple sizes or shapes for treating different soft tissues in different parts of the body. For example, one embodiment of the cutting device 700 may be sized for cutting the A1 pulley for treating trigger finger, and another embodiment may be sized for cutting the carpal ligament for treating carpal tunnel syndrome. Thus, the example dimensions provided above are for exemplary purposes only and should not be interpreted as limiting the scope.

Referring now to FIGS. 9A-9I (side views) and 10A-10I (perspective views), a method of cutting soft tissue using the soft tissue cutting device 700 will be described. Although the cutting device 700 will be described here for use in cutting the A1 pulley in a finger of a hand to treat trigger finger, the soft tissue cutting device 700 may alternatively be used to cut one or more other pulleys in the finger (A2-A5) or to cut soft tissue(s) in other parts of the hand or wrist, such as but not limited to a carpal tunnel release procedure. For trigger finger treatment, typically only the A1 pulley is cut, but the soft tissue cutting device 700 may also be used to cut the A2 pulley or even the A3, A4 or A5 pulley, if necessary. The method, or any portion(s) of the method, may be performed using ultrasound guidance, for example via a handheld ultrasound wand applied to the hand. In FIGS. 9A-9I and 10A-10I, the method is illustrated without showing the user's hand or the patient's hand, for clarity of illustration.

Before performing the trigger finger release procedure, the physician user will typically position the patient's hand on a stable surface, palm side up, and prepare the hand with drapes, sterilization, local anesthesia, marking of anatomical landmarks, etc. As the trigger finger release procedure begins, at throughout the procedure, the physician may use ultrasound guidance, typically with an ultrasound device positioned on the skin of the patient's hand, to follow the location of the soft tissue cutting device 700 and/or to visualize structures in the hand. This part of the procedure—ultrasound guidance—may be performed throughout the entire procedure or during one or more parts of the procedure, and any suitable ultrasound device may be used. The use of ultrasound will not be described in further detail below.

Figure 9A:
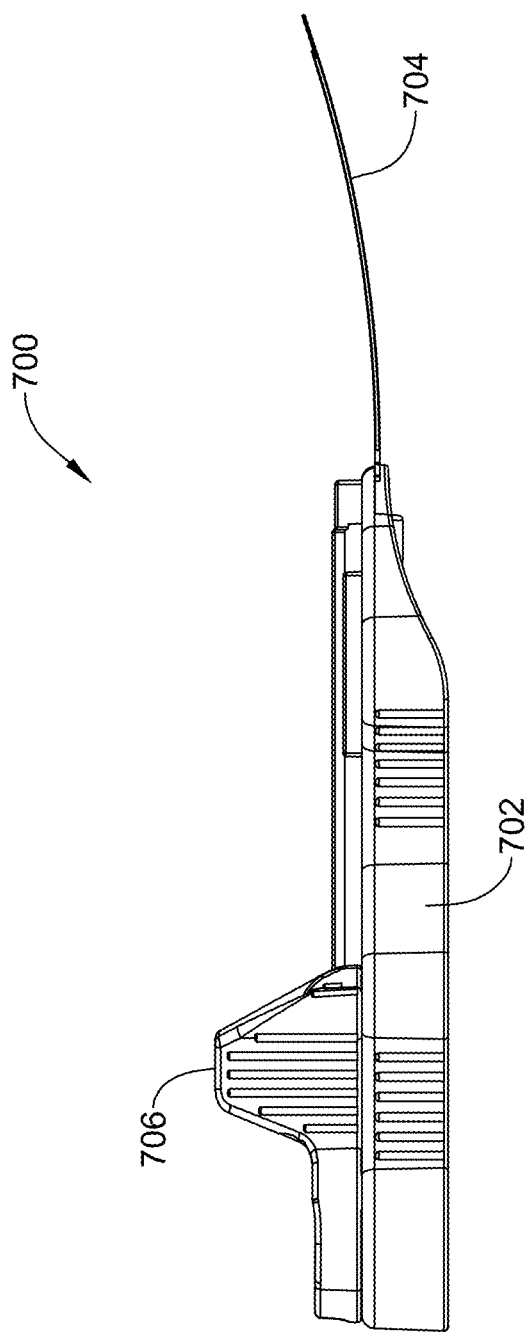
FIGS. 9A-9I are side views of the soft tissue cutting device of FIGS. 7-8D, illustrating a method of using the device.

Step one of a method for cutting an A1 pulley (or other pulley(s)) to treat trigger finger is illustrated in FIGS. 9A (side view) and 10A (perspective view). In this step, the soft tissue cutting device 700 is held in the locked position, with the slider 706 locked to the handle 702 via the aperture 712 and the locking feature 710 (see FIG. 10A). Usually but not necessarily, the physician user will advance the introducer shaft 704 into the patient's hand/finger while the device 700 is in this locked position (or "safety position"). (The step of introducing the introducer shaft 704 into the hand is not pictured here.) In the embodiment shown, the physician will have made a small incision (or "stab incision") in the palm of the hand or the finger, proximal to the A1 pulley, so that the distal end 727 of the introducer shaft 704 can be advanced through the small incision. In alternative embodiments, where the distal end 727 is sharp and functions as a blade, the distal end 727 may be used to puncture through the patient's skin, thus eliminating the need for an incision beforehand. Again, in this embodiment, the introducer shaft 704 is advanced into the hand with the soft tissue device 700 in the locked/safety position. In alternative embodiments, the cutting device 700 may first be placed in a ready position (as described below) before advancing the introducer shaft 704 into the hand/finger.

Figure 9B:
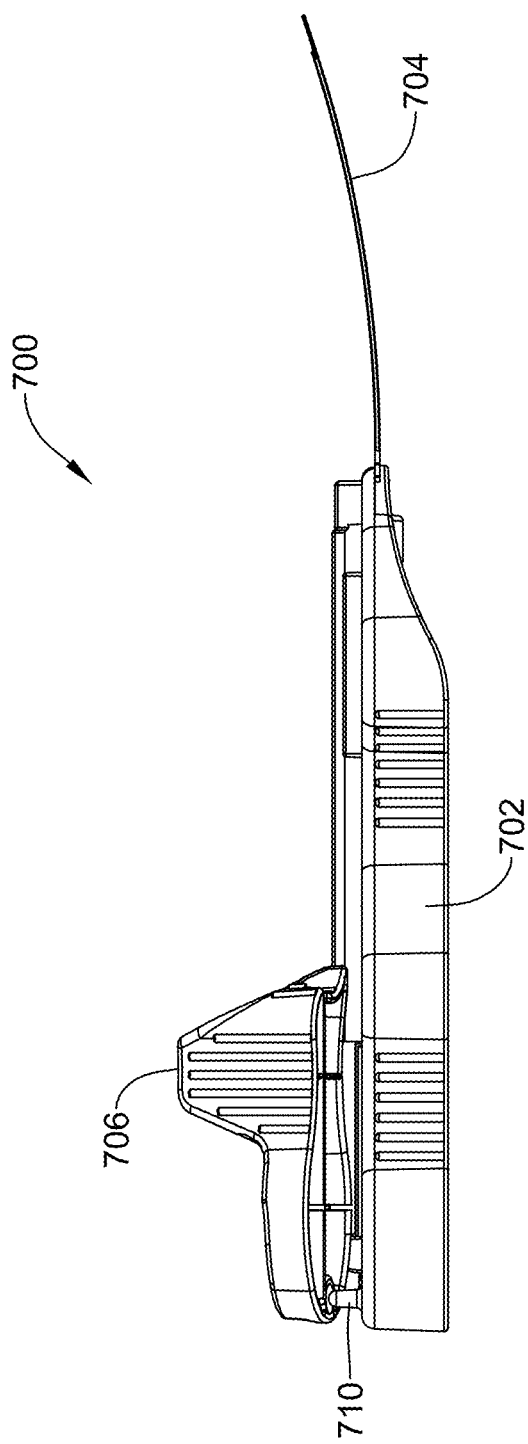
Figure 10A:
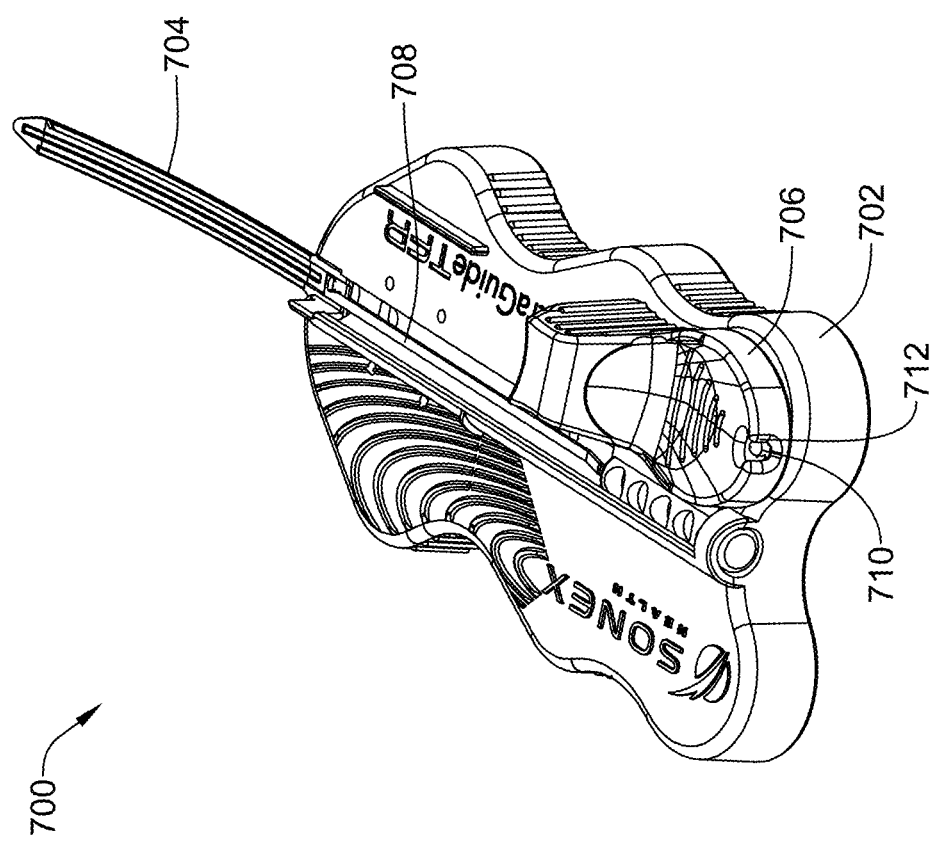
FIGS. 10A-10I are perspective views of the soft tissue cutting device, illustrating the same method as in FIGS. 9A-9I.
Figure 10B:
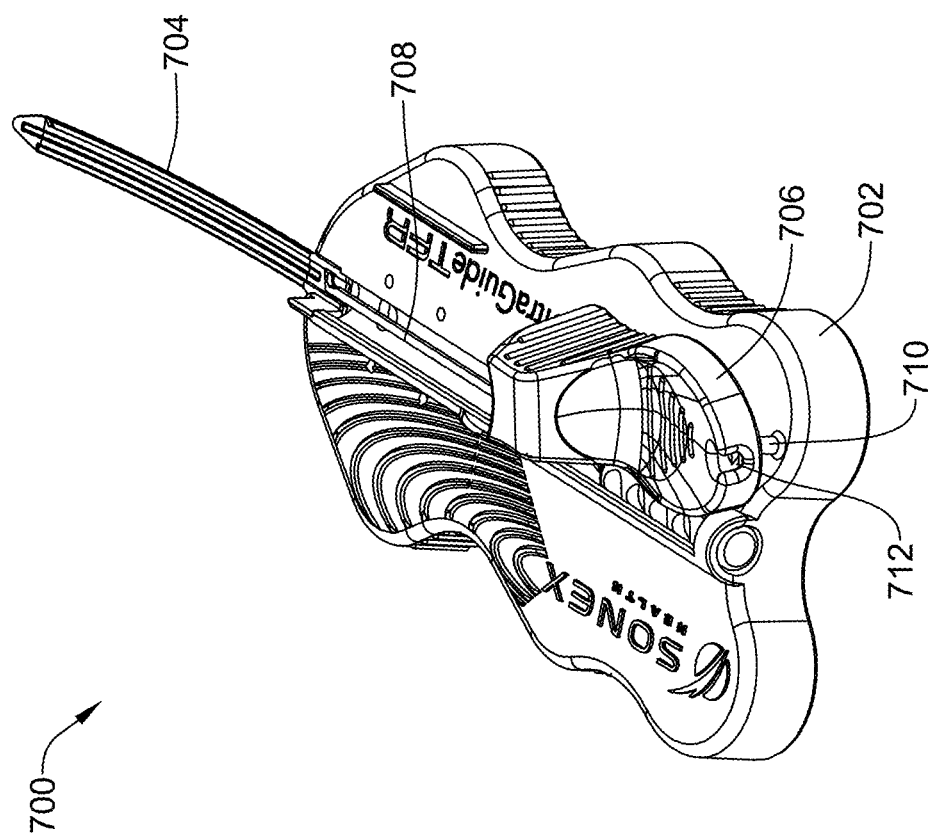

In step two of the method, illustrated in FIGS. 9B and 10B, the user rotates the slider 706 upward, to raise the slider 706 (and the aperture 712) up off the locking feature 710. (In alternative embodiments, any size, shape, or type of locking feature(s) may be included on the soft tissue cutting device 700 to lock the slider 706 to the handle 702.)

Figure 9C:
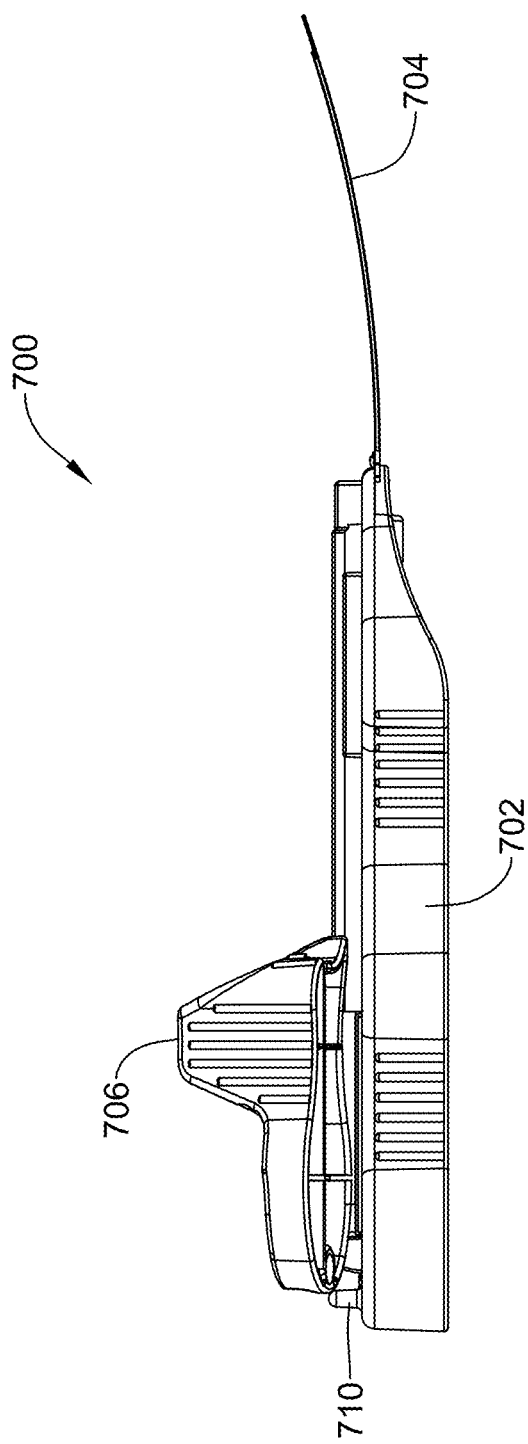
Figure 10C:
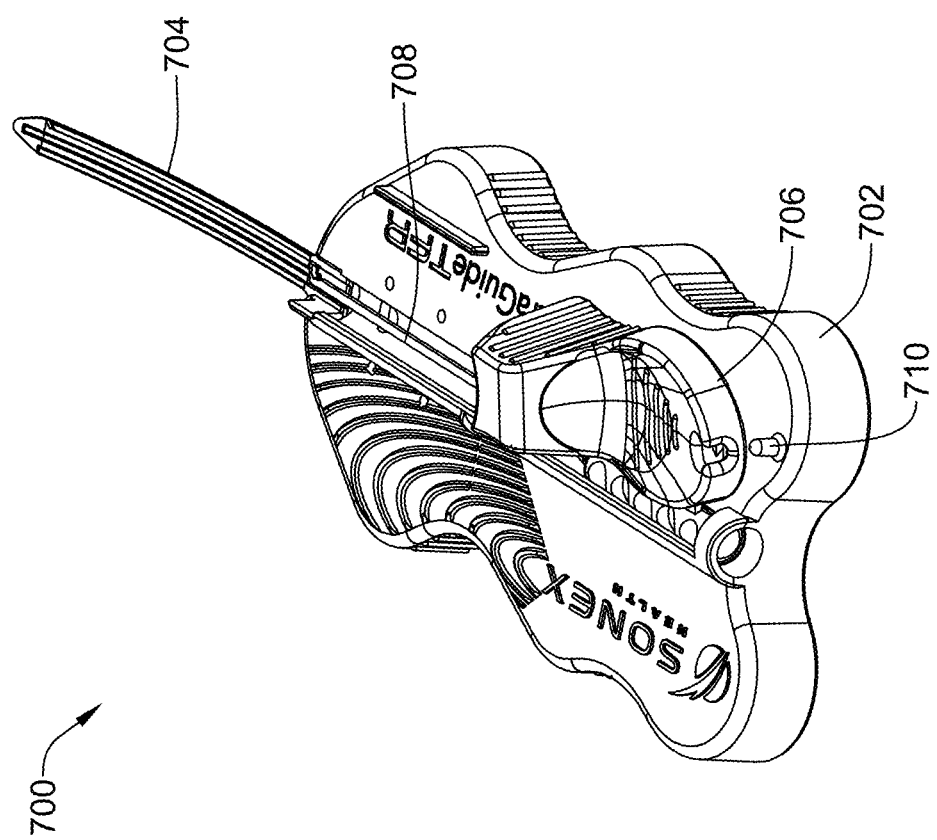

In step three, illustrated in FIGS. 9C and 10C, the user slides the upwardly rotated slider 706 a small distance forward (in a distal direction), at least far enough so that the aperture 712 is completely past/distal to the locking feature 710.

Figure 9D:
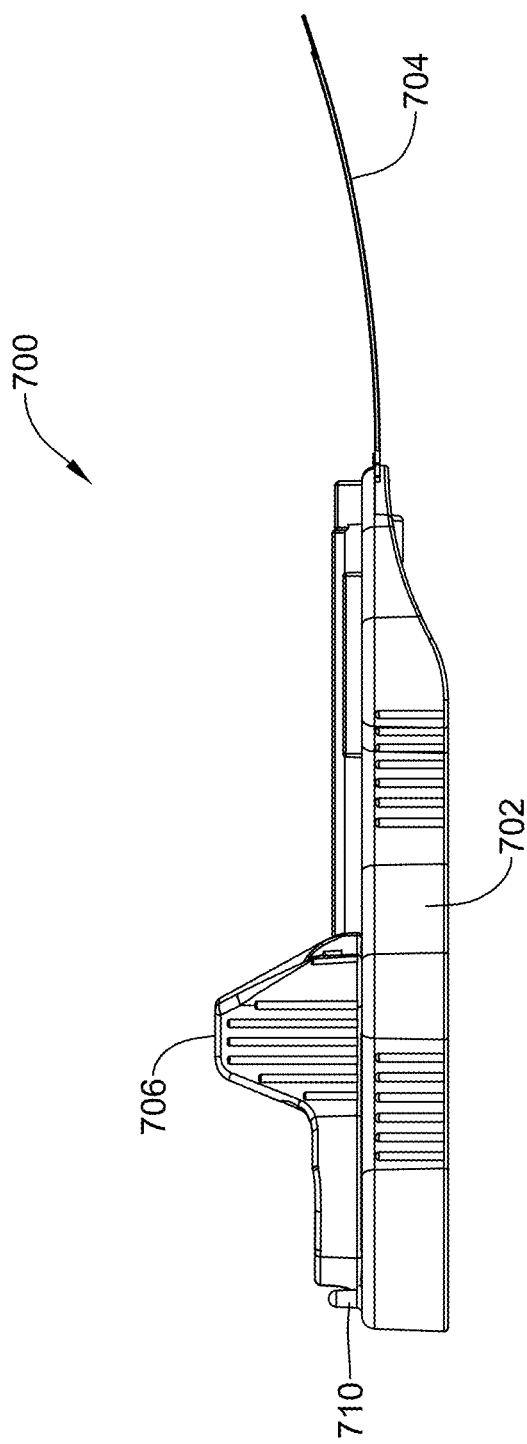
Figure 10D:
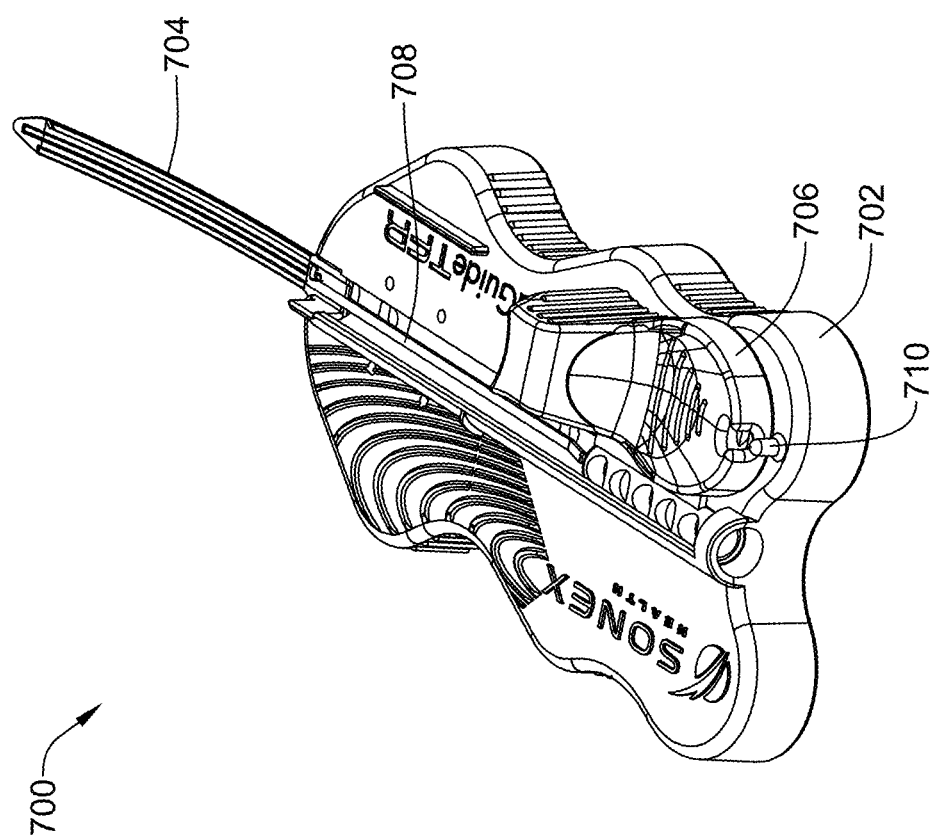
Figure 10E:
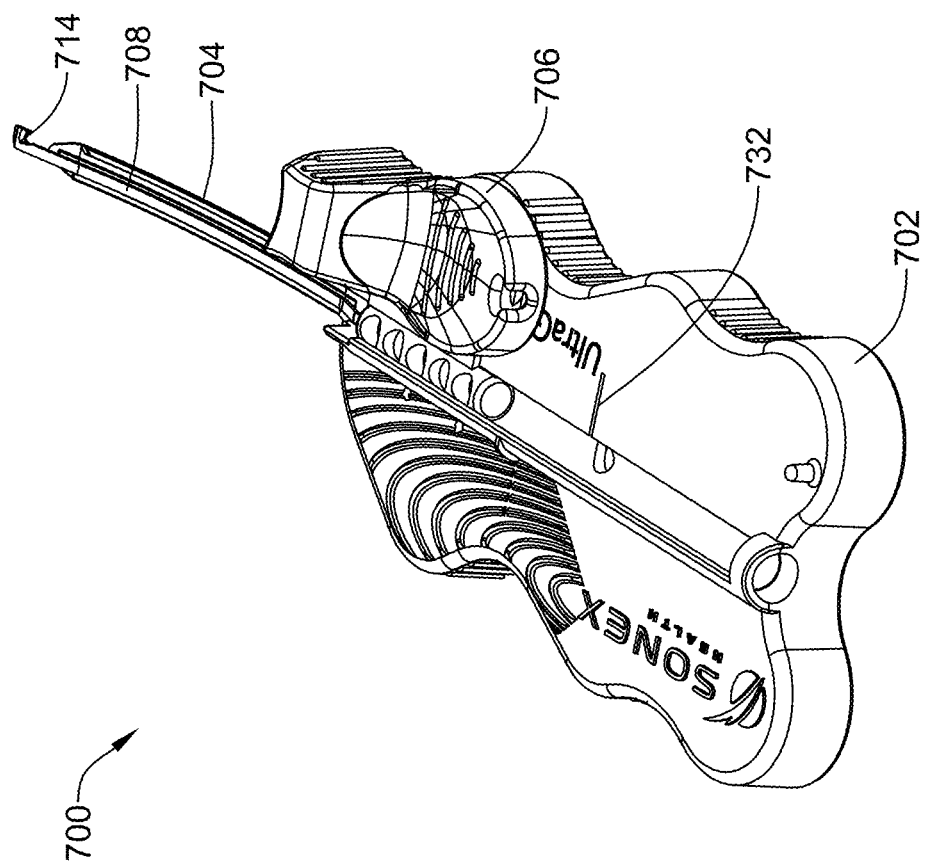
Figure 10F:
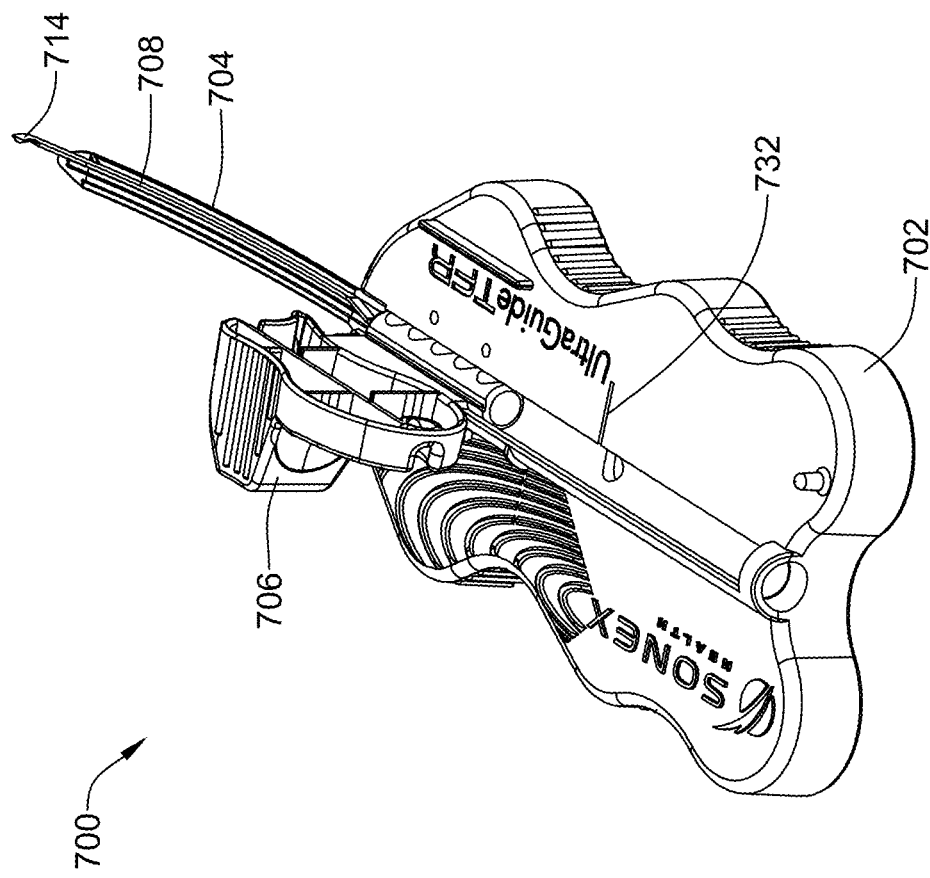
Figure 10G:
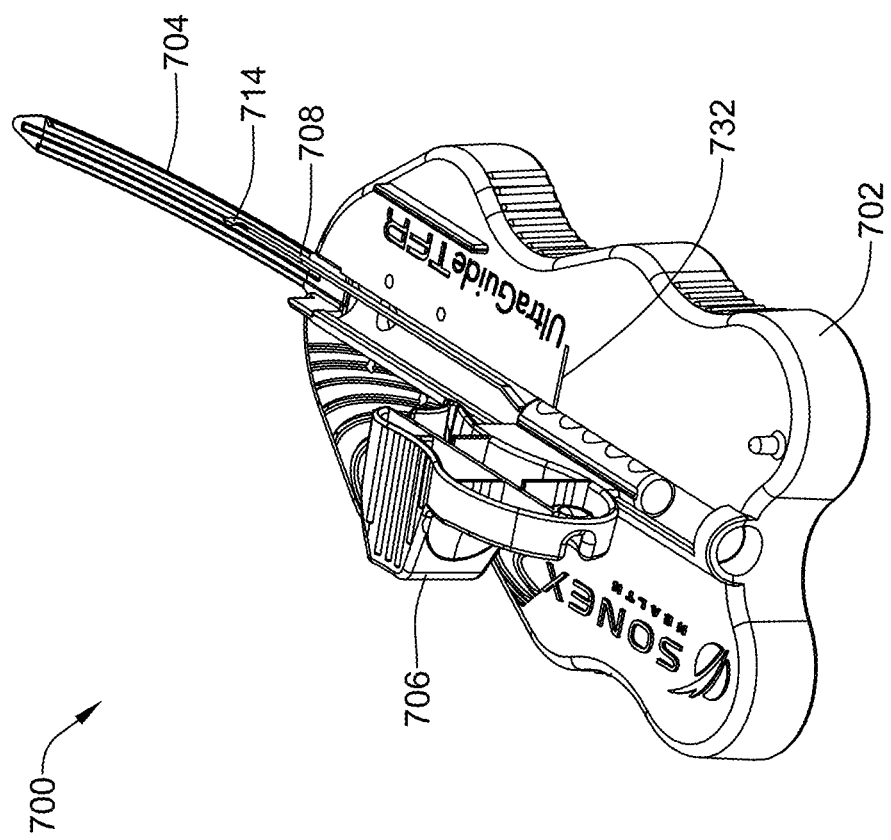

In step four, shown in FIGS. 9D and 10D, the user then rotates the slider 706 back down onto the upper surface of the handle 702. The cutting device 700 is now in the "ready position" (i.e., the unlocked or activated position), meaning that the cutting device 700 is ready to cut soft tissue. In some embodiments, the upper surface of the handle 702 may include one or more indicator marks 732 (FIGS. 10E-10G). In the embodiment shown, the indicator mark 732 indicates to a user when the front end of the slider 706 is in the ready/start position and the end/finish position. As mentioned above, in some embodiments the soft tissue cutting device 700 may first be placed in this ready position before advancing the introducer shaft 704 into the hand, although this might not be recommended for safety reasons. Also as mentioned above, the location of the introducer shaft 704 in a desired position for cutting the A1 pulley may be confirmed at this point of the procedure using an externally located ultrasound device. Once the introducer shaft 704 is positioned below the A1 pulley and the distal end 727 is located distal to the A1 pulley, the user moves to the next step.

Figure 9E:
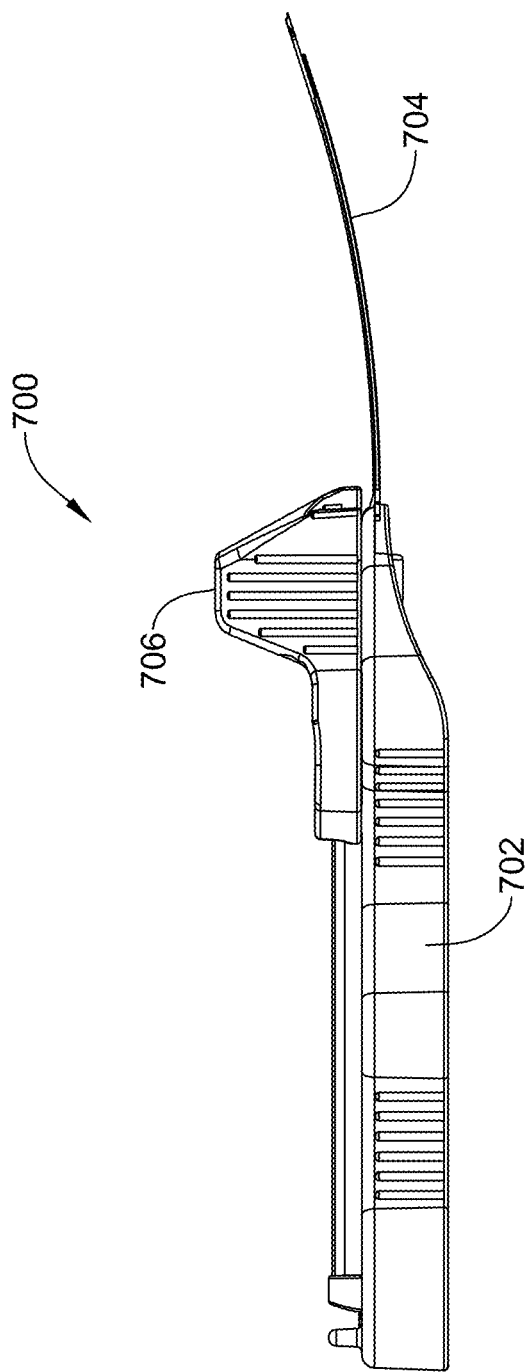

In step five, illustrated in FIGS. 9E and 10E, the user advances the slider 706 distally along the handle 702 to advance the blade 708 along the guiding channel 723 of the introducer shaft 704. The slider is advanced in the "down" or flat position, so the blade 708 is also down/flat along the guiding channel 723. The user advances the slider 706 until the distal end of the blade 708 is at or near the distal end 727 of the introducer shaft 704. In this position, the cutting surface 714 of the blade 708 will be distal to the A1 pulley.

Figure 9F:
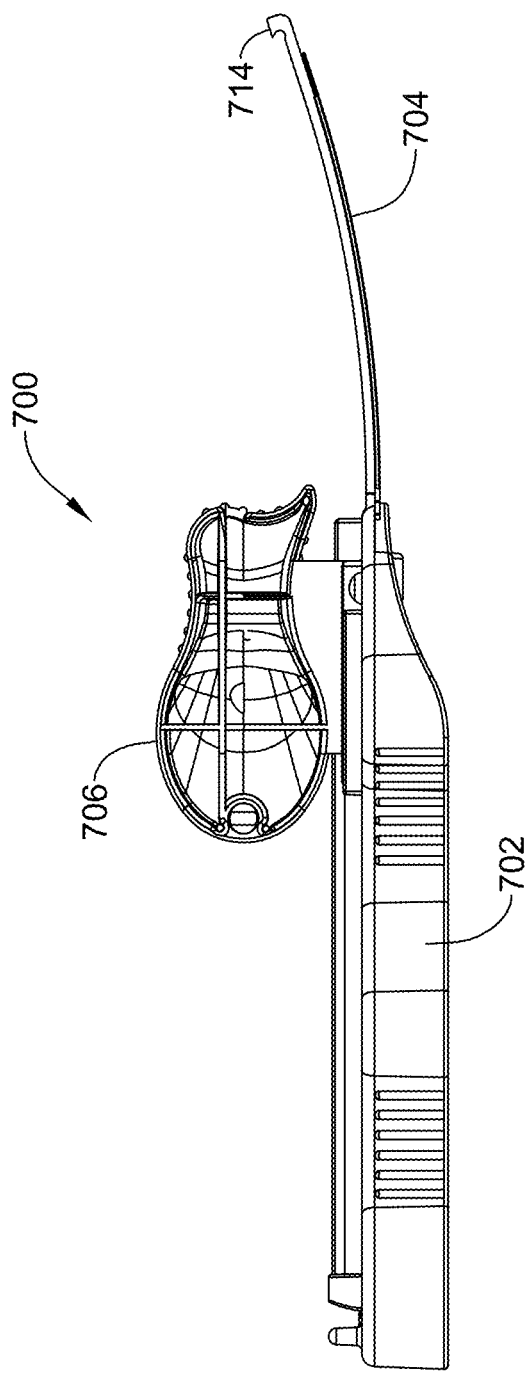

Next, in step six, illustrated in FIGS. 9F and 10F, the user rotates the slider 706 upward to rotate the blade 708 and the cutting surface 714 upward. In this position, a bottom of the blade 708 may rest in the rotating channel 725. This may be referred to as the cutting position, blade active position, or blade vertical position, in which the blade 708 and the cutting surface 714 are oriented perpendicular or near perpendicular to the flat upper surface of the introducer shaft 704.

Figure 9G:
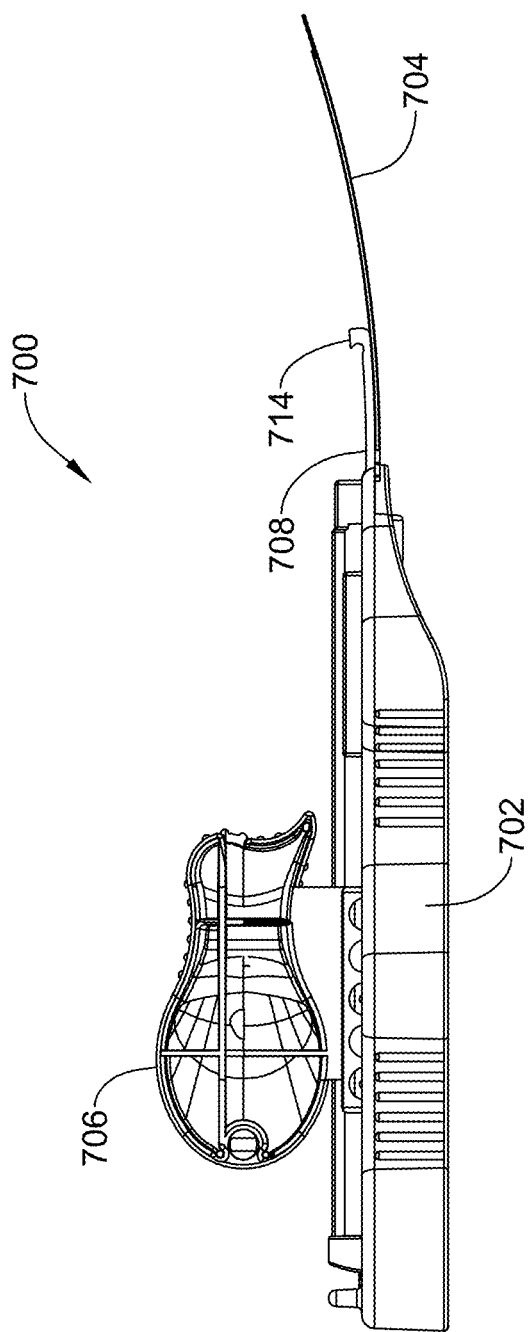

As shown in FIGS. 9G and 10G, step seven involves retracting/sliding the slider 706 proximally along the handle 702, while maintaining the slider 706 in the cutting/vertical position, to cut the A1 pulley (and/or other pulley(s) or other soft tissues) in the finger. The user may choose to use the indicator mark 732 on the upper surface of the handle 702 to know how far back to slide the slider 706 to complete the cutting step. When the slider reaches the indicator mark 732, this indicates to the user that the target tissue has been cut and it is not necessary to retract the slider 706 further proximally. Other suitable indicator marks may include a mark showing when the blade 708 is fully advanced to the end of the introducer shaft 704.

Figure 9H:
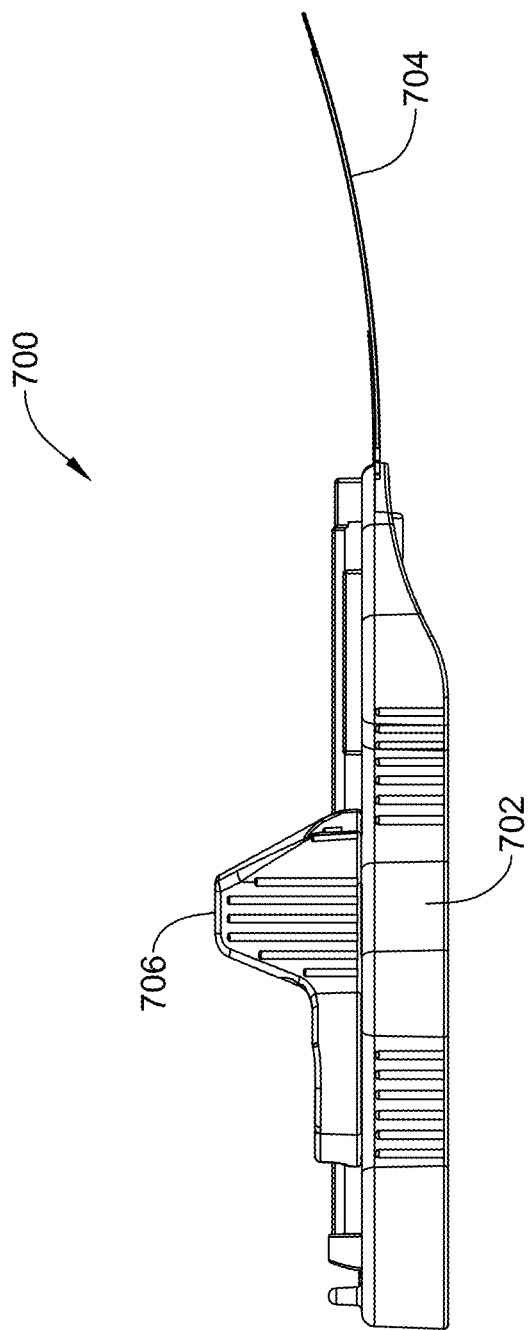
Figure 10H:
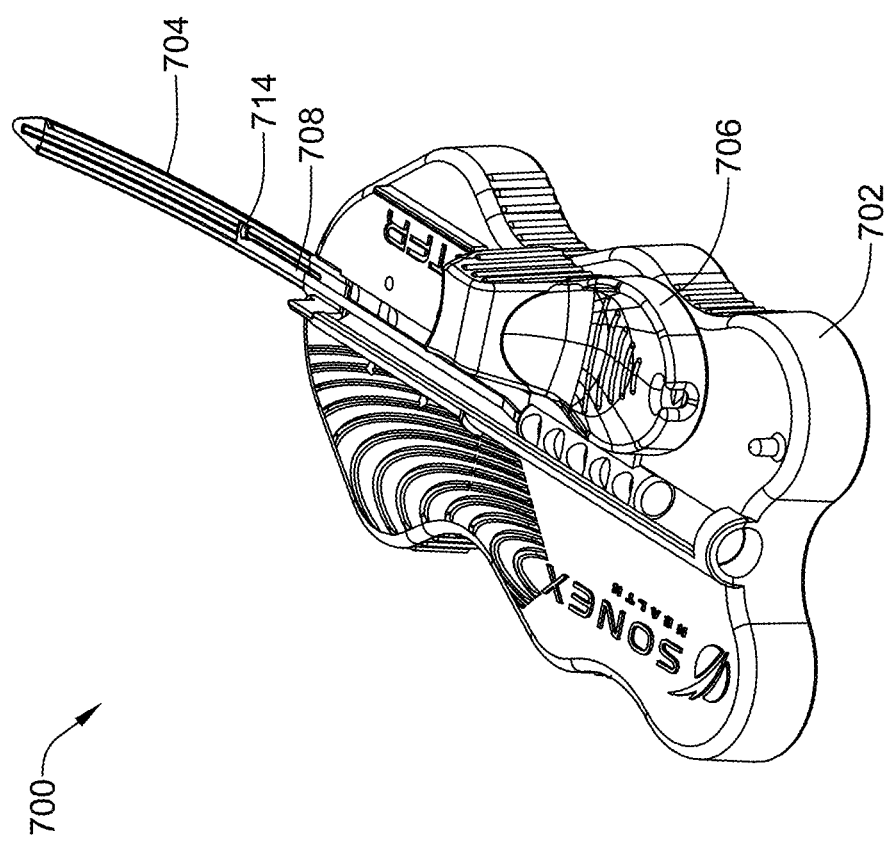

In step eight, illustrated in FIGS. 9H and 10H, the user rotates the slider 706 back down to the upper surface of the handle 702, thus flattening the blade 708 to an inactive, non-cutting position. In some cases, the introducer shaft 704 of the soft tissue cutting device 700 may be withdrawn from the patient's hand at this point.

Figure 9I:
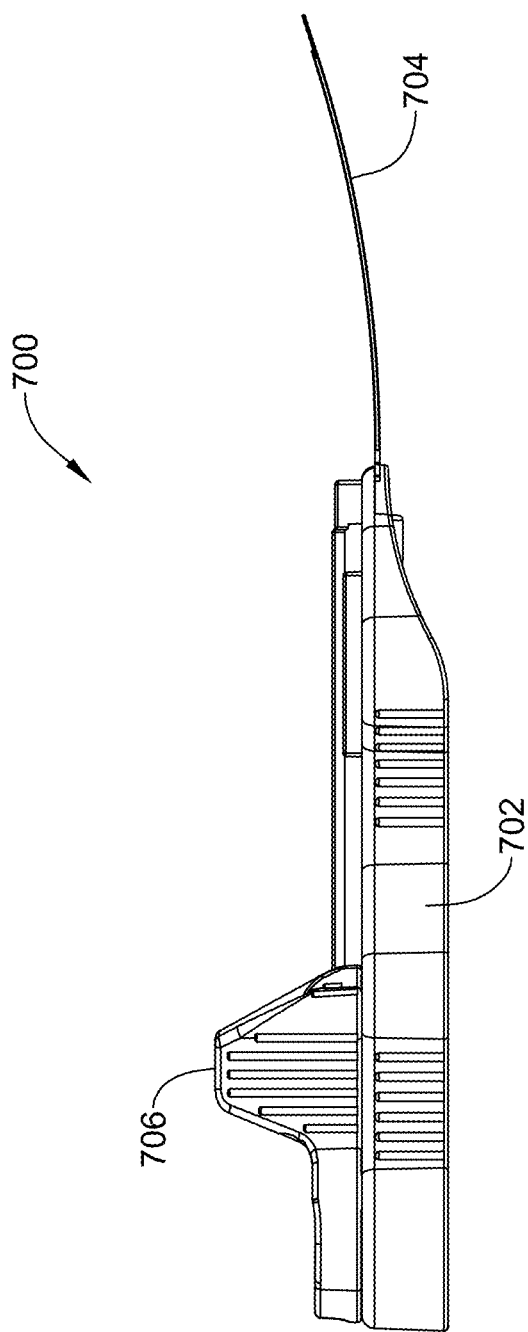
Figure 10I:
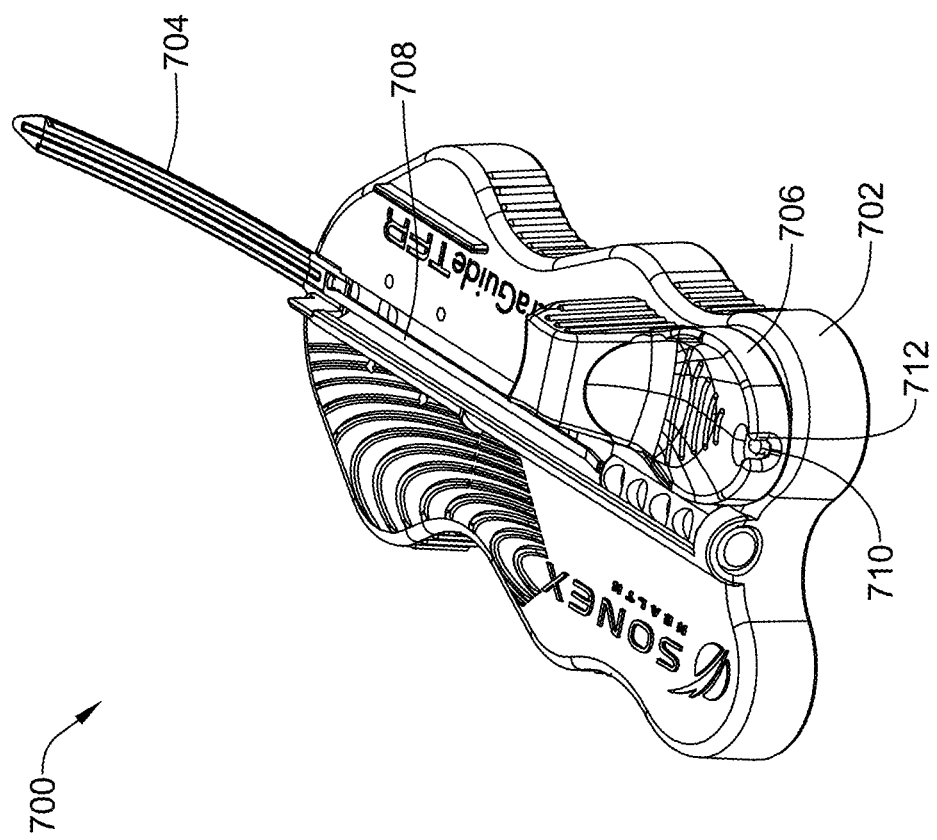

Finally, in step nine, illustrated in FIGS. 9I and 10I, the user repositions the slider 706 in the locked position relative to the handle 702. The user may wait until the cutting device 700 is in this locked/safety position before withdrawing the cutting device 700 from the patient's hand. Locking the cutting device 700 before withdrawing it from the hand may be safer than withdrawing the cutting device 700 in an unlocked configuration. After this last step, the soft tissue cutting device 700 may sometimes be used in a different location on the same patient. In other cases, a new cutting device 700 is used for each new location and soft tissue on the same patient. Once the procedure is complete, the cutting device 700 may be disposed of in a safe manner. The cutting device 700 should never be used in multiple patients, unless a reusable, sterilizable embodiment of the device is provided and sterilized between uses.

Figure 11A:
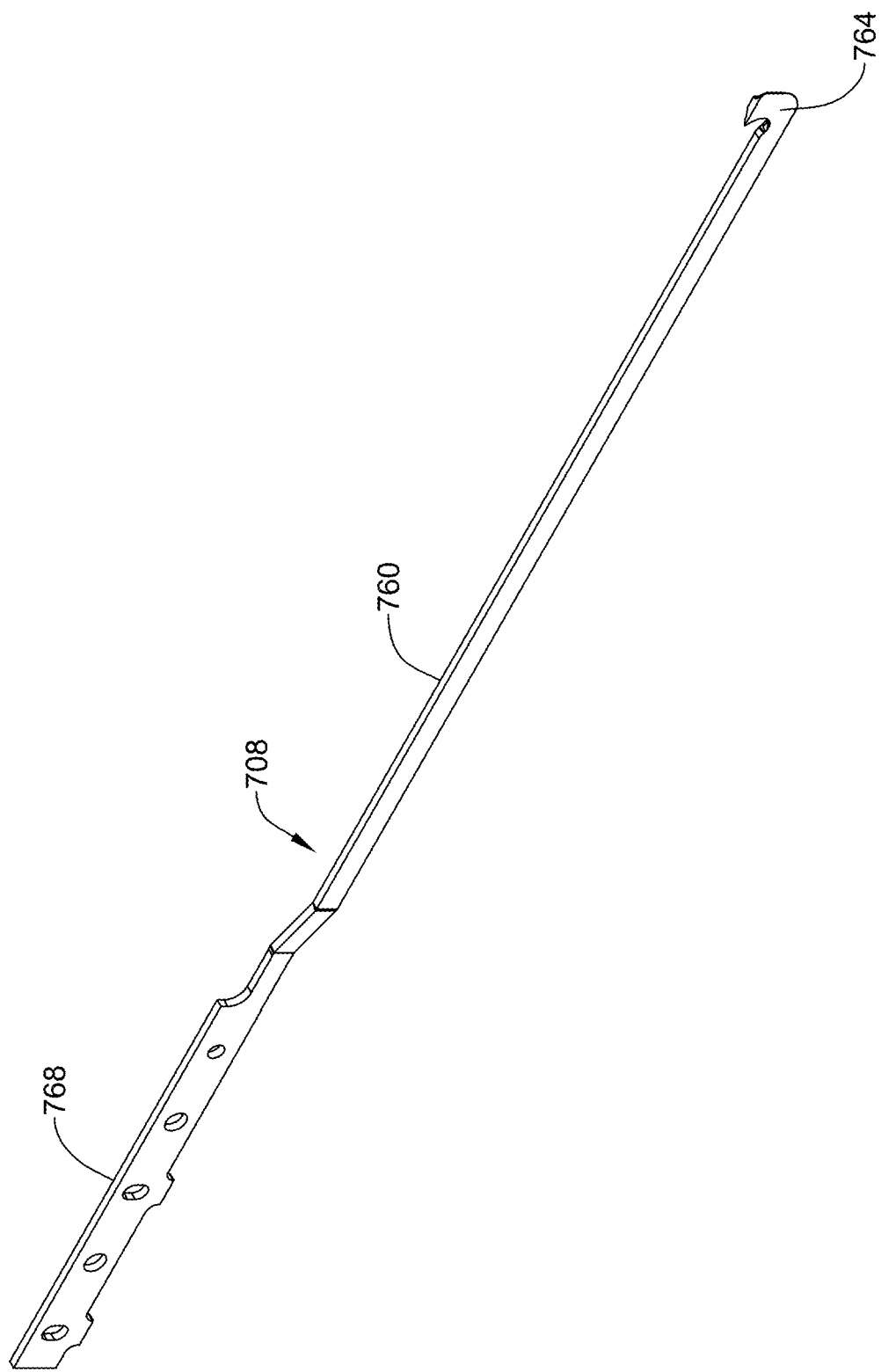
FIGS. 11A and 11B are two opposite side perspective views of the blade of the soft tissue cutting device of FIGS. 7-8D.
Figure 11B:
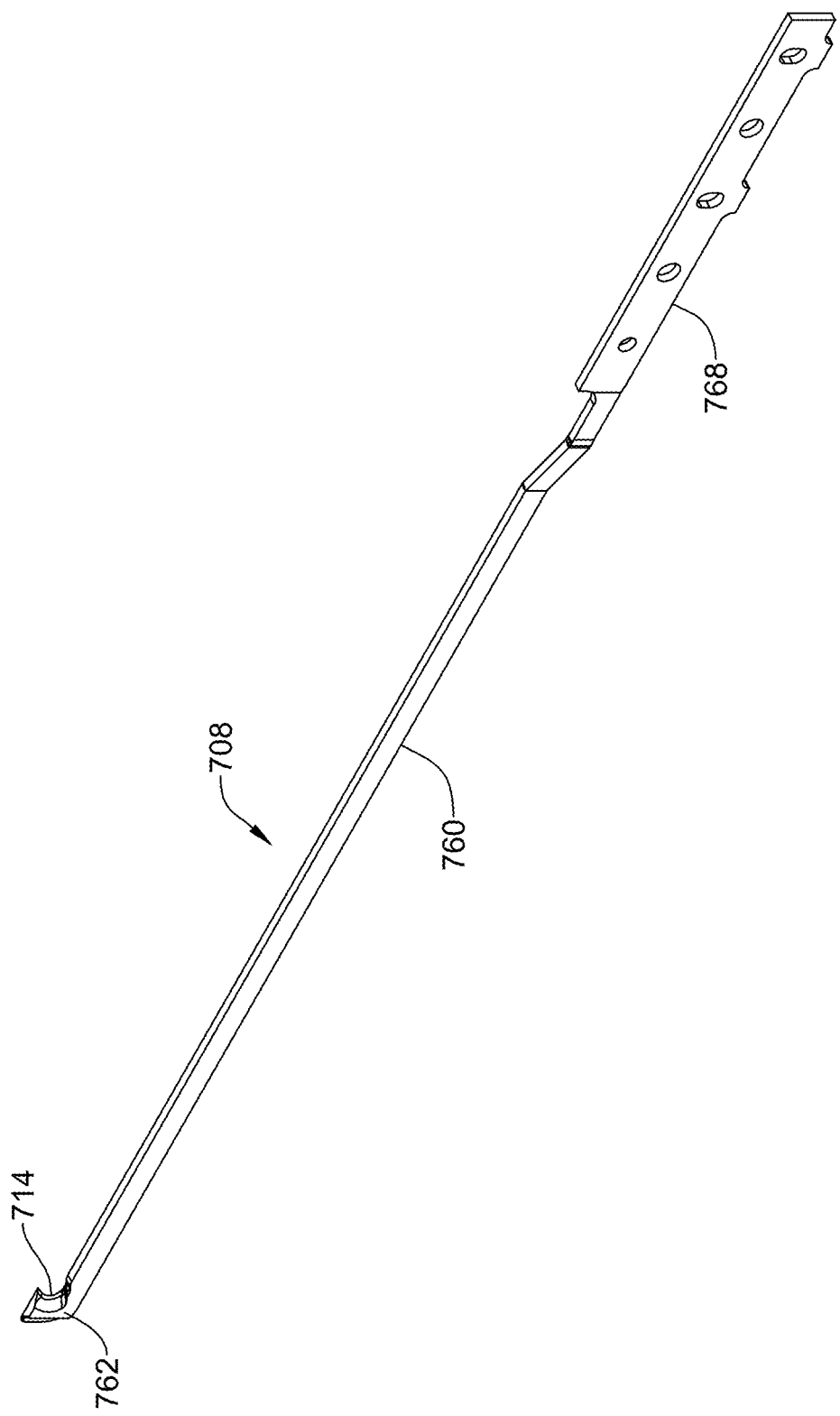
Figure 11C:
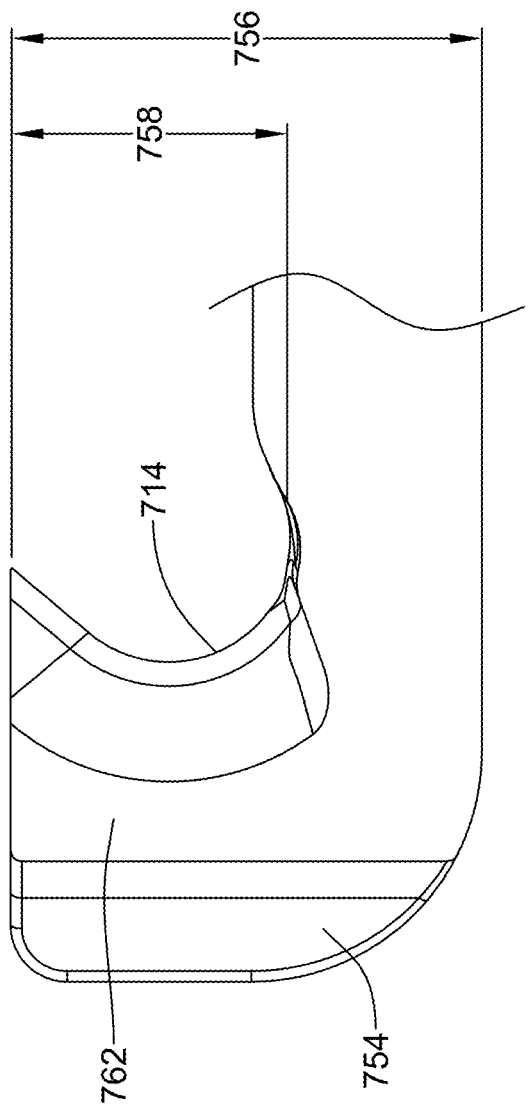
FIG. 11C is a close-up, side view of a distal end cutting portion of the cutting blade, from the circled portion of FIG. 11B.

Referring now to FIGS. 11A-11C, additional details of the blade 708 are shown, according to one embodiment. In this embodiment, the blade 708 includes a blade shaft 760, a cutting surface 714, a beveled distal side 762, a flat distal side 764, and a handle attachment portion 768. The beveled distal side 762 and the flat distal side 764 form the cutting surface 714 is a single sided cutting edge. In alternative embodiments, both distal sides 762, 764 may be beveled, to form a double-sided cutting edge. FIG. 11C is a detailed view of the beveled distal side 762, shown from the perspective of the circled portion of FIG. 11B labeled "A". In this embodiment, the beveled distal side includes the cutting surface 714 (or "cutting edge") and a distal beveled edge 754, both of which may be used for cutting soft tissue. The blade 708 has a total height 756, measured from the bottom of the blade shaft 760 to the highest point on the blade 708, and a blade height 758 (or "cutting surface height"), measured from the lowest point of the cutting surface 714 to the highest point of the cutting surface 714. In various embodiments, the total height 756 may be from about 0.05 inch to about 1 inch, or in some cases from about 0.06 inch to about 0.1 inch, and in one embodiment about 0.085 inch. The blade height 758 may be from about 0.02 inch to about 0.5 inch, or in some embodiments from about 0.03 inch to about 0.08 inch, and in one embodiment about 0.047 inch. As with previously listed dimensions, these dimensions are provided as examples only and should not be interpreted as limiting the scope of this disclosure.

While embodiments of the invention have been described, various changes, adaptations and modifications may be made, without departing from the spirit of the invention and the scope of the appended claims.

We claim:

1. A method of cutting soft tissue in a hand of a patient, the method comprising:
   advancing a shaft of an introducer into the patient's hand so that a distal end of the shaft is located beyond an A1 pulley in a finger of the hand;
   sliding a slider along a handle coupled with the shaft of the introducer, to advance a flat blade, which is coupled with the slider, along an upper flat surface of a guiding channel on the shaft to position a cutting surface of the flat blade beyond the A1 pulley, wherein the flat blade lies in a first plane, and the upper flat surface of the guiding channel lies in a second plane parallel with and below the first plane, and wherein the flat blade comprises a one-piece construction;
   rotating the slider up off the handle to rotate the flat blade into a third plane that is angled relative to the second plane, to position the cutting surface of the flat blade in a cutting orientation;
   retracting the slider in its rotated orientation to pull the flat blade proximally to cause the cutting surface to cut the A1 pulley; and
   removing the introducer and the flat blade from the patient's hand.

2. The method of claim 1, further comprising using an ultrasound device to confirm a location of the shaft of the introducer in the patient's hand.

3. The method of claim 1, wherein the introducer and the flat blade are separate devices.

4. A method of cutting soft tissue in a hand to treat trigger finger, the method comprising:
   advancing an introducer shaft of a soft tissue cutting device into the hand to position a distal end of the introducer shaft beyond a pulley in a finger of the hand;
   advancing a flat blade of the soft tissue cutting device along a guiding channel on an upper surface of the introducer shaft by sliding a slider along a handle coupled with the introducer shaft, to position a distal end of the flat blade at or near the distal end of the introducer shaft, wherein the flat blade lies in a first plane, and the upper surface of the introducer shaft lies in a second plane parallel with and below the first plane, and wherein the flat blade comprises a one-piece construction;
   rotating the slider up off the handle to rotate a cutting surface of the flat blade to an orientation at or near perpendicular relative to the upper surface of the introducer shaft;
   retracting the slider in its rotated orientation to pull the flat blade along the introducer shaft to cut the pulley; and
   removing the introducer shaft and the blade from the hand.

5. The method of claim 4, further comprising rotating the slider back down onto the handle after cutting the pulley to position the flat blade in an inactive position, before removing the introducer shaft and the flat blade from the hand.

6. The method of claim 4, wherein the soft tissue cutting device further comprises a locking mechanism for locking the slider in an inactive position on the handle, the method further comprising unlocking the slider from the inactive position before advancing the flat blade.

7. The method of claim 6, further comprising locking the slider in the inactive position before removing the introducer shaft and the flat blade from the hand.

8. The method of claim 6, wherein the handle includes at least one marker to indicate a location for the slider in a ready position, the method further comprising positioning the slider at the location for the ready position before advancing the flat blade.

9. The method of claim 4, wherein the pulley comprises an A1 pulley.

10. The method of claim 4, further comprising visualizing at least one of the introducer shaft or the flat blade inside the hand, using an ultrasound device positioned outside the hand.

* * * * *